(12) United States Patent
Jamison et al.

(10) Patent No.: US 9,382,281 B2
(45) Date of Patent: Jul. 5, 2016

(54) NICKEL PRE-CATALYSTS AND RELATED COMPOSITIONS AND METHODS

(71) Applicant: Massachusetts Institute of Technology, Cambridge, MA (US)

(72) Inventors: Timothy F. Jamison, Somerville, MA (US); Eric Alan Standley, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/535,854

(22) Filed: Nov. 7, 2014

(65) Prior Publication Data

US 2015/0141684 A1 May 21, 2015

Related U.S. Application Data

(60) Provisional application No. 61/902,484, filed on Nov. 11, 2013.

(51) Int. Cl.
*C07F 15/04* (2006.01)
*B01J 31/24* (2006.01)

(52) U.S. Cl.
CPC .................. *C07F 15/04* (2013.01); *B01J 31/24* (2013.01); *B01J 31/2409* (2013.01); *B01J 31/2414* (2013.01); *B01J 2231/34* (2013.01); *B01J 2531/847* (2013.01)

(58) Field of Classification Search
CPC ... C07F 15/04; B01J 31/2409; B01J 31/2414; B01J 31/24
USPC ........................................................ 556/21, 23
See application file for complete search history.

(56) References Cited

U.S. PATENT DOCUMENTS

| 3,887,441 A | 6/1975 | Hughes et al. |
| 2009/0043052 A1 | 2/2009 | McCullough et al. |
| 2010/0063287 A1* | 3/2010 | Annis ............................. 546/4 |
| 2010/0197920 A1 | 8/2010 | Ying et al. |

OTHER PUBLICATIONS

Lanni et al., Macromolecules, vol. 43, pp. 8039-8044 (2010).*
Tsou et al., J. Org. Chem., vol. 45, No. 10, pp. 1930-1937 (1980).*
Invitation to Pay Additional Fees mailed Jan. 16, 2015 for Application No. PCT/US2014/064565.
International Search Report and Written Opinion mailed Apr. 15, 2015 for Application No. PCT/US2014/064565.
[No Author Listed] Chlorobis(dicyclohexylphenylphosphino)(2-methylphenyl)nickel(II). Product Detail. Strem Chemicals. 2013.
[No Author Listed] Phosphine Ligand Application Guide. Sigma-Aldrich. 2012.
Chatt et al., Alkyls and aryls of transition metals. Part III. Nickel(II) derivatives. J. Chem. Soc. 1960:1718-29.
Chen et al., Ni(II)-(sigma-aryl) complex: a facile, efficient catalyst for nickel-catalyzed carbon-nitrogen coupling reactions. J Org Chem. Aug. 3, 2007;72(16):6324-7. Epub Jul. 11, 2007.

(Continued)

*Primary Examiner* — Porfirio Nazario Gonzalez
(74) *Attorney, Agent, or Firm* — Wolf, Greenfield & Sacks, P.C.

(57) ABSTRACT

Described herein are nickel pre-catalysts and related compositions and methods. The nickel pre-catalysts may be activated to form catalysts which may be utilized in organic reactions.

29 Claims, 7 Drawing Sheets

Monodentate Phosphines

Bidentate Phosphines

X = Cl or Br.
R = optionally substituted alkyl or optionally substituted aryl

(56) References Cited

OTHER PUBLICATIONS

Fache et al., Nitrogen-containing ligands for asymmetric homogeneous and heterogeneous catalysis. Chem Rev. Jun. 14, 2000;100(6):2159-231.

Fortman et al., N-Heterocyclic carbene (NHC) ligands and palladium in homogeneous cross-coupling catalysis: a perfect union. Chem Soc Rev. Oct. 2011;40(10):5151-69. doi: 10.1039/c1cs15088j.

Gual et al., Phosphorus(III) Ligands in Homogeneous Catalysis: Design and Synthesis. John Wiley and Sons. 2012:81-131.

Guo et al., Comparing Nickel- and Palladium-Catalyzed Heck Reactions. Organometallics. Mar. 27, 2004;23(9):2114-23.

Heck et al., Palladium-catalyzed vinylic hydrogen substitution reactions with aryl, benzyl, and styryl halides. J. Org. Chem. Jul. 1972;37(14):2320-2.

Henry et al., Hydroxyproline-derived pseudoenantiomeric [2.2.1] bicyclic phosphines: asymmetric synthesis of (+)- and (−)-pyrrolines. J Am Chem Soc. Aug. 27, 2014;136(34):11890-3. doi: 10.1021/ja505592h. Epub Aug. 14, 2014.

Herrmann et al., Bis-triphenylphosphin-nickel-äthylen and analoge Komplexe. Angew. Chem. Sep. 7, 1962;74(17):693-4.

Herrmann et al., N-heterocyclic carbenes: a new concept in organometalliccatalysis. Angew Chem Int Ed Engl. Apr. 15, 2002;41(8):1290-309.

Ho et al., Alpha-olefins as alkenylmetal equivalents in catalytic conjugate addition reactions. Angew Chem Int Ed Engl. 2008;47(10):1893-5. doi: 10.1002/anie.200705163.

Ho et al., Highly Selective Coupling of Alkenes and Aldehydes Catalyzed by [Ni(NHC){P(OPh)$_3$}]: Synergy between a Strong δ Donor and a Strong π Acceptor. Angew. Chem. Int. Ed. Jan. 22, 2007;46(5):782-5.

Ittel et al., Late-metal catalysts for ethylene homo- and copolymerization. Chem Rev. Apr. 12, 2000;100(4):1169-203.

Laus et al., N,N'-Di(alkyloxy)imidazolium Salts: New Patent-free Ionic Liquids and NHC Precatalysts. Z. Naturforsch. 2007;62b:295-308.

Matsubara et al., Nickel-catalyzed allylic substitution of simple alkenes. J Am Chem Soc. May 26, 2010;132(20):6880-1. doi: 10.1021/ja101186p.

Matsubara et al., Nickel-catalyzed Heck-type reactions of benzyl chlorides and simple olefins. J Am Chem Soc. Nov. 30, 2011;133(47):19020-3. doi: 10.1021/ja209235d. Epub Nov. 8, 2011.

Mizoroki et al., Arylation of Olefin with Aryl Iodide Catalyzed by Palladium. Bull. Chem. Soc. Jap. 1971;44:581.

Molinaro et al., Nickel-catalyzed reductive coupling of alkynes and epoxides. J Am Chem Soc. Jul. 9, 2003;125(27):8076-7.

Ng et al., Highly enantioselective and regioselective nickel-catalyzed coupling of allenes, aldehydes, and silanes. J Am Chem Soc. May 25, 2005;127(20):7320-1.

Ng et al., Nickel-catalyzed coupling of terminal allenes, aldehydes, and silanes. Tetrahedron. 2006;62(49):11350-9.

Pasto, A theoretical study of disproportionation reactions of diimide (N2H2) species. J. Am. Chem. Soc. Nov. 1979;101(23):6852-7.

Patel et al., Asymmetric catalytic coupling of organoboranes, alkynes, and imines with a removable (trialkylsilyloxy)ethyl group—direct access to enantiomerically pure primary allylic amines. Angew Chem Int Ed Engl. Jul. 26, 2004;43(30):3941-4.

Pfaltz, From Corrin Chemistry to Asymmetric Catalysis—A Personal Account. Synlett. 1999;(S1):835-42.

Rasappan et al., Metal-bis(oxazoline) complexes: From coordination chemistry to asymmetric catalysis. Coordination Chemistry Reviews. 2008;252(5-7):702-14.

Standley, Simplifying Nickel(0) Catalysis, Air Stable Nickel Precatalysts for C—C Bond Construction. PowerPoint Presentation. Boise State University. Feb. 8, 2013.

Standley et al., A Broadly Applicable Strategy for Entry into Homogeneous Nickel(0) Catalysts from Air-Stable Nickel(II) Complexes. Organometallics. Apr. 28, 2014;33(8):2012-2018. Epub Apr. 16, 2014.

Standley et al., Simplifying nickel(0) catalysis: an air-stable nickel precatalyst for the internally selective benzylation of terminal alkenes. J Am Chem Soc. Jan. 30, 2013;135(4):1585-92. doi: 10.1021/ja3116718. Epub Jan. 14, 2013.

Stone et al., Some Nickel(II) Complexes Containing the Ligands Cyclohexyldiphenylphosphine, Dicyclohexylphenylphosphine and Tricyclohexylphosphine. Inorg. Chim. Acta 1970;5(3):434-8.

Tolman, Steric effects of phosphorus ligands in organometallic chemistry and homogeneous catalysis. Chem. Rev. 1977;77(3):313-48.

* cited by examiner

Monodentate Phosphines

Bidentate Phosphines

X = Cl or Br.
R = optionally substituted alkyl or optionally substituted aryl

*multiply-substituted and heteroaromatic* trans-(PCy$_2$Ph)$_2$Ni(o-tolyl)Cl (1)

trans-(PCy$_2$Ph)$_2$NiCl$_2$ (4)

PBn₃ (106)

PMe₂Ph (109)

(S)-BINAP (115)

dcpf (117)

Xantphos (118)

pyphos (119)

NICKEL PRE-CATALYSTS AND RELATED COMPOSITIONS AND METHODS

RELATED APPLICATIONS

The present application claims priority under 35 U.S.C. §119(e) to U.S. provisional application, U.S. Ser. No. 61/902,484, filed Nov. 11, 2013, entitled "Nickel Pre-Catalysts and Related Compositions and Methods", incorporated herein by reference.

STATEMENT REGARDING FEDERALLY SPONSORED RESEARCH OR DEVELOPMENT

This invention was made with government support under Grant No.R01 GM063755 awarded by the National Institutes of Health. The government has certain rights in the invention.

FIELD OF INVENTION

Described herein are nickel pre-catalysts and related compositions and methods.

BACKGROUND

Homogeneous nickel catalysts are useful for a wide variety of carbon-carbon and carbon-heteroatom bond forming organic reactions. Nickel, a base metal, is a low-cost, versatile, and attractive metal for use in catalytic transformations. One barrier to the wider adoption of homogeneous nickel catalysis for synthesis, however, is the difficulty and cost of synthesizing and handling nickel(0) sources and the phosphine ligands often used in conjunction with such complexes. Accordingly, improved catalysts are needed.

SUMMARY OF THE INVENTION

Described herein are nickel pre-catalysts and related compositions and methods.

In some embodiments, pre-catalysts are provided. In some embodiments, a pre-catalyst comprises a nickel (II) atom, wherein the nickel (II) atom is associated with at least one phosphine ligand; at least one aryl ligand; and at least one leaving group. In another embodiment, a pre-catalyst comprises a nickel (II) atom, wherein the nickel (II) atom is associated with at least one N-heterocyclic carbene ligand; at least one aryl ligand; and at least one leaving group.

In some embodiments, methods are provided. In some embodiments, a method comprises activating a pre-catalyst as described herein. In some cases, the method may further comprise reacting an optionally substituted benzyl chloride with a terminal alkene in the presence of the catalyst. In other cases, the method may further comprise reacting a terminal alkene with an aldehyde and a silyl triflate in the presence of the catalyst.

Other advantages and novel features of the present invention will become apparent from the following detailed description of various non-limiting embodiments of the invention when considered in conjunction with the accompanying figures. Unless otherwise noted, all references cited herein are incorporated by reference in their entirety. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
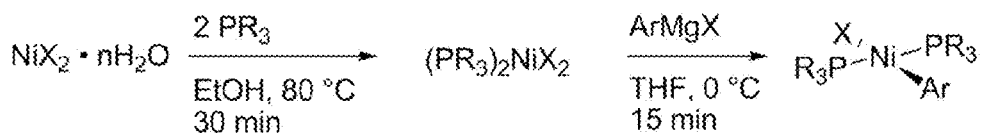
FIG. 1 illustrates non-limiting methods of forming pre-catalysts, according to some embodiments.
Figure 1:
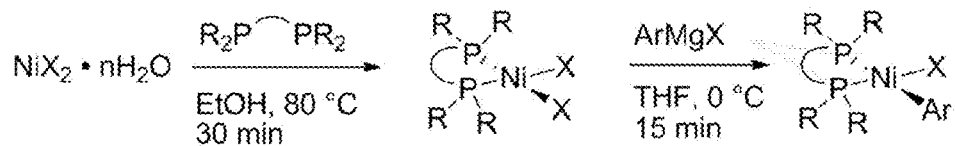

Described herein are nickel pre-catalysts and related compositions and methods. The pre-catalysts may be activated, as described herein, and employed in organic reactions. In some embodiments, the nickel pre-catalyst is air stable. In some embodiments, the nickel pre-catalyst comprises a nickel (II) atom. In some embodiments, the nickel pre-catalyst is a four coordinate complex. In some embodiments, the nickel pre-catalysts or activated catalysts therefrom provide a number of advantages over current nickel pre-catalysts/catalysts, including air stability, low molecular weight, high activity, ease of synthesis, low cost starting materials, ease of activation of the pre-catalyst, and/or application in a wide variety of organic reactions.

In some embodiments, the nickel pre-catalysts described herein are stable and isolable. A "stable, isolable compound" refers to isolated reaction products and does not refer to unstable intermediates or transition states. As used herein, a "pre-catalyst" refers to a chemical species which, upon activation, may produce an active catalyst species in a reaction. The catalyst precursor may be isolated as a stable compound and, in some cases, may be converted in situ into the active form of the catalyst. As used herein, the term "catalyst" includes active forms of the catalyst participating in the reaction.

In some embodiments, a nickel pre-catalyst comprises a nickel (II) atom, wherein the nickel (II) atom is associated with at least one dative ligand, at least one aryl ligand, and at least one leaving group. In some embodiments, the nickel pre-catalyst is associated with at least two dative ligands. In some cases, the nickel (II) atom is associated with two dative ligands, an aryl ligand, and a leaving group. Non-limiting examples of dative ligands include phosphine ligands, phosphite ligands, N-heterocyclic carbene ligands, and nitrogen ligands. Dative ligands are known in the art, for example, see Hartwig, J. F. Organotransition Metal Chemistry, from Bonding to Catalysis; University Science Books: New York, 2010, Chapter 2, Sections 2.3-2.7, 33-64. In some embodiments, the nickel pre-catalyst does not comprise cyclooctadiene (COD) and/or is not formed from $Ni(COD)_2$. In some embodiments, at least one of the ligands is chiral.

In some embodiments, a nickel pre-catalyst comprises a nickel (II) atom, wherein the nickel (II) atom is associated with at least one phosphine ligand, at least one aryl ligand, and at least one leaving group. In some cases, the nickel pre-catalyst is associated with at least two phosphine ligands. In some cases, the nickel (II) atom is associated with two phosphine ligands, an aryl ligand, and a leaving group. In other embodiments, a nickel pre-catalyst comprises a nickel (II) atom, wherein the nickel (II) atom is associated with at least one phosphite ligand, at least one aryl ligand, and at least one leaving group. In some cases, the nickel pre-catalyst is associated with at least two phosphite ligands. In some cases, the nickel (II) atom is associated with two phosphite ligands, an aryl ligand, and a leaving group. In some cases, the nickel (II) atom is associated with a phosphite ligand, a phosphine ligand, an aryl ligand, and a leaving group. In yet other embodiments, a nickel pre-catalyst comprises a nickel (II) atom, wherein the nickel (II) atom is associated with at least one nitrogen ligand, at least one aryl ligand, and at least one leaving group. In some cases, the nickel pre-catalyst is associated with at least two nitrogen ligands. In some cases, the nickel (II) atom is associated with two nitrogen ligands, an aryl ligand, and a leaving group. In some cases, the nickel (II) atom is associated with a nitrogen ligand, a phosphine ligand, an aryl ligand, and a leaving group. In still yet other embodiments, a nickel pre-catalyst comprised a nickel (II) atom, wherein the nickel (II) atom is associated with at least one N-heterocyclic carbene ligand, at least one aryl ligand, and at least one leaving group. In some cases, the nickel (II) atom is associated with at least one N-heterocyclic carbene ligand, at least one phosphine ligand, at least one aryl ligand, and at least one leaving group. In some cases, the nickel pre-catalyst comprises two N-heterocyclic carbene ligands. In some cases, the nickel (II) atom is associated with an N-heterocyclic carbene ligand, a phosphine ligand, an aryl ligand, and a leaving group. Each of the ligands will now be described in detail.

In some embodiments, the nickel pre-catalyst comprises at least one phosphine ligand. The phosphine ligand(s) may be monodentate or bidentate. In some cases, the nickel pre-catalyst comprises at least two phosphine ligands. In some embodiments, the nickel pre-catalyst comprises two phosphine ligands. In embodiments where the nickel pre-catalyst comprises two phosphine ligands, the two phosphine ligands may be cis or trans. In some cases, the two phosphine ligands are trans. In some cases, the two phosphine ligands are cis. In some cases, the nickel pre-catalyst comprises one bidentate phosphine ligand. In embodiments wherein the nickel pre-catalyst comprises a bidentate phosphine ligand, the phosphine atoms may be cis or trans. In some cases wherein the nickel pre-catalyst comprises a bidentate phosphine ligand, the phosphine atoms are cis. In other cases wherein the nickel pre-catalyst comprises a bidentate phosphine ligand, the phosphine atoms are trans.

In some embodiments, the at least one phosphine ligand is monodentate. In embodiments wherein the nickel pre-catalyst comprises at two monodentate phosphine ligands, the phosphine ligand may be trans or cis. In some cases, the two monodentate phosphine ligands are trans. In other cases, the two monodentate phosphine ligands are cis. In some embodiments, each monodentate phosphine ligand is the same or different and has the structure $P(R^1)_3$, wherein each $R^1$ is independently optionally substituted alkyl, optionally substituted cycloalkyl, or optionally substituted aryl, or any two $R^1$ may be joined together to form a ring. In some embodiments, each monodentate phosphine ligand is the same or different and has the structure $P(R^1)_3$, wherein each $R^1$ is independently optionally substituted alkyl, optionally substituted cycloalkyl, or optionally substituted aryl. In some embodiments, each $R^1$ is alkyl, optionally substituted. In some embodiments, each $R^1$ is cycloalkyl, optionally substituted. In some embodiments, each $R^1$ is aryl, optionally substituted. In some embodiments, at least one $R^1$ is cyclohexyl. In some embodiments, each $R^1$ is cyclohexyl. In some embodiments, at least one $R^1$ is phenyl. In some embodiments, each $R^1$ is phenyl. In some embodiments, at least one $R^1$ is alkyl. In some embodiments, each $R^1$ is alkyl. In some embodiments, the one or more phosphine ligands are independently selected from the group consisting of $PPh_3$, $PCyPh_2$ (Cy=cyclohexyl), $PCy_2Ph$, $PCy_3$, PCyp (Cyp=cyclopentyl), $PBn_3$ (Bn=benzyl), $PMe_2Ph$, $PEt_3$, and $P(nBu)_3$. Other monodentate phosphine ligands are known in the art, for example, see Tolman, Chemical Reviews, 77(3), 1977, 313-348, herein incorporated by reference.

In some embodiments, the phosphine atom of the monodentate phosphine is present in a bicyclic heterocycle. For example, the monodentate phosphine may comprises 2-phosphabicyclo[2.2.1]heptane or 7-phosphabicyclo[2.2.1]heptane, or substituted version thereof. Other non-limiting examples of bicyclic heterocycles comprising at least one phosphine atom will be known to those of ordinary skill in the art. In some embodiments, the bicyclic heterocycle comprising at least one phosphine atom may further comprise one or more other heteroatoms, for example, nitrogen, oxygen, or sulfur. Non-limiting examples of bicyclic heterocycles comprising at least one phosphine atom include:

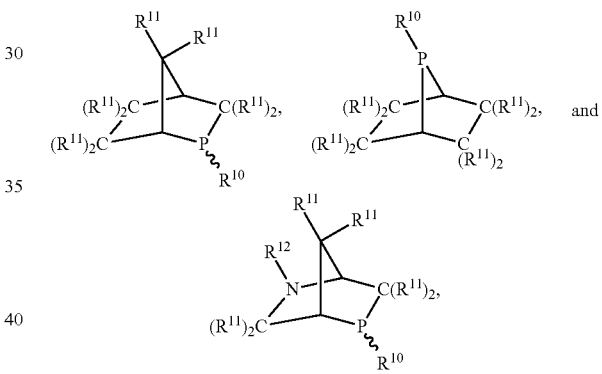

wherein each $R^{10}$ is independently optionally substituted alkyl, optionally substituted cycloalkyl, or optionally substituted aryl, each $R^{11}$ is independently hydrogen, optionally substituted alkyl, optionally substituted heteroalkyl, optionally substituted cycloalkyl, optionally substituted aryl, or optionally substituted heteroaryl, and $R^{12}$ is independently optionally substituted alkyl, optionally substituted cycloalkyl, optionally substituted aryl, or a nitrogen-protection group (e.g., tosyl, mesyl, etc.). In some embodiments, $R^{10}$ is aryl. In some embodiments, $R^{10}$ is phenyl. In some embodiments, each $R^{11}$ is hydrogen. In some embodiments, at least one $R^{11}$ is not hydrogen.

In some embodiments, the at least one phosphine ligand is bidentate. In some embodiments, the bidentate phosphine ligand has the structure $(R^2)_2P—(R^3)_n—P(R^2)_2$, wherein each $R^2$ is independently optionally substituted alkyl, optionally substituted cycloalkyl, or optionally substituted aryl, or any two $R^2$ could be joined together to form a ring, each $R^3$ is —O—, optionally substituted alkylene, optionally substituted heteroalkylene, optionally substituted arylene, optionally substituted heteroarylene, or optionally substituted ferrocenylene, and n is 1, 2, 3, 4, 5, or 6. In some embodiments, each $R^2$ is independently optionally substituted alkyl, optionally substituted cycloalkyl, or optionally substituted aryl. In some embodiments, each R² is cycloalkyl, optionally substituted. In some embodiments, each R² is aryl, optionally substituted. In some embodiments, at least one R² is cyclohexyl. In some embodiments, each R² is cyclohexyl. In some embodiments, at least one R² is phenyl. In some embodiments, each R² is phenyl. In some embodiments, at least one R² is alkyl. In some embodiments, each R² is alkyl. In some embodiments, at least one R³ is alkylene. In some embodiments, at least one R³ is ferrocenylene (e.g., —(C₅H₅)—Fe—(C₅H₅)—). In some embodiments, at least one R³ is arylene. In some embodiments, the bidentate ligand is independently selected from the group consisting of 1,2-bis(diphenylphosphino)ethane (dppe), 1,3-bis(diphenylphosphino)propane (dppp), 1,4-bis(diphenylphosphino)butane (dppb), 2,2'-bis(diphenylphosphino)-1,1'-binaphthyl (BINAP), 1,1'-bis(diphenylphosphino)ferrocene (dppf), 1,1'-bis(dicyclohexylphosphino)ferrocene (dcpf), 9,9-dimethyl-4,5-bis(diphenylphosphino)xanthene (xantphos), and 2-[2-(diphenylphosphino)ethyl]pyridine (pyphos). Other bidentate phosphine ligands are known in the art, for example, see Tolman, Chemical Reviews, 77(3), 1977, 313-348, herein incorporated by reference.

In some embodiments, the pre-catalyst comprises at least one phosphite ligand. In some embodiments, phosphite ligand may be monodentate. In other embodiments, the phosphite ligand is bidentate. In embodiments, wherein the nickel pre-catalyst comprises at two monodentate phosphite ligands, the phosphite ligands may be trans or cis. In some cases, the two phosphite ligands are trans. In other cases, the two phosphite ligands are cis. In some embodiments, each monodentate phosphite ligand is the same or different and has the structure P(OR⁸)₃, wherein each R⁸ is independently optionally substituted alkyl, optionally substituted cycloalkyl, or optionally substituted aryl, or optionally, any two R⁸ may be joined together to form a ring. In some cases, each R⁸ is independently optionally substituted alkyl, optionally substituted cycloalkyl. In some embodiments, the bidentate phosphite ligand has the structure (R⁸)₂OP—O(R⁹)ₙO—PO(R⁸)₂, wherein each R⁸ is independently optionally substituted alkyl, optionally substituted cycloalkyl, or optionally substituted aryl, or any two R⁸ may be joined together to form a ring; each R⁹ is —O— optionally substituted alkylene, optionally substituted heteroalkylene, optionally substituted arylene, optionally substituted heteroarylene, or optionally substituted ferrocenylene; and n is 1, 2, 3, 4, 5, or 6. In some embodiments, each R⁸ is independently optionally substituted alkyl, optionally substituted cycloalkyl, or optionally substituted aryl. In some embodiments, the phosphite ligand is as known in the art, for example, see Gual et al., Phosphorus (III) Ligands in Homogenous Catalysis: Design and Synthesis, John Wiley and Sons, 2012, 81-131, herein incorporated by reference.

In some embodiments, the nickel pre-catalyst comprises at least one N-heterocyclic carbene ligand. In some embodiments, the N-heterocyclic carbene ligand has the structure:

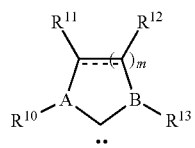

wherein each R¹¹⁻¹³ is independently absent, hydrogen, optionally substituted alkyl, optionally substituted cycloalkyl, optionally substituted heteroalkyl, optionally substituted cycloheteroalkyl, optionally substituted aryl, or optionally substituted heteroaryl, or wherein any two of R¹¹⁻¹³ are joined to form a optionally substituted cycloalkyl, optionally substituted cycloheteroalkyl, optionally substituted aryl, or optionally substituted heteroaryl; A is carbon or a heteroatom; B is a heteroatom; ⩵ is a single bond or double bond; and m is an integer between 1 and 3. In some embodiments, A and B are each N. In some embodiments, m is 1. In some embodiments, m is 2. In some embodiments, m is 3. In some embodiments, the N-heterocyclic carbene ligands is as known in the art, for example, see Herrmann, Angew. Chem. Int. Ed., 47, 2002, 1290-1309; and Fortman et al, Chem. Soc. Rev., 40, 2011, 5151-5169, each herein incorporated by reference.

In some embodiments, the nickel pre-catalyst comprises at least one nitrogen ligand. A nitrogen ligand is a ligand which coordinates to the nickel (II) atom via a nitrogen atom. Non-limiting example of nitrogen ligands include, for example, 2,2'-bipyridine and substituted versions thereof, 1,10-phenanthroline and derivatives and substituted versions thereof, oxazoline-based ligands, (e.g., bisoxazoline), pyridine-based ligands (e.g., pyridine bisoxazoline and substituted versions thereof), and 1,2-diimino ligands. In some embodiments, the nitrogen-based ligand is as known in the art, for example, see Rasappan et al., Coordination Chemistry Reviews, 252, 2008, 702-714; Pfaltz, Synlett, S1, 1999, 835-842; Fache et al., Chem. Rev., 100, 2000, 2159-2231; and Ittel et al., Chemical Reviews, 100, 2000, 1169-1203, each herein incorporated by reference.

In some embodiments, the nickel pre-catalyst comprises at least one aryl ligand. Generally, the aryl ligand comprises an optionally substituted aromatic carbocyclic group in which at least one of the carbon atoms is associated with the nickel (II) atom. The aryl ligand may have a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). In some embodiments, the aryl ligand is optionally substituted phenyl. In some embodiments, the aryl ligand comprises the structure (C₆(R⁵)₅), wherein each R⁵ is the same or different and is selected from the group consisting of hydrogen or optionally substituted alkyl. In some embodiments, at least on R⁵ is not hydrogen. In some embodiments, at least two R⁵ are not hydrogen. In some embodiments, at least one ortho position is substituted. In some embodiments, both ortho positions are substituted. In some embodiments, at least one ortho position is not hydrogen. In some embodiments, both ortho positions are not hydrogen. Non-limiting examples of aryl ligands include tolyl (e.g., ortho-tolyl), 2,4,6-triisopropylphenyl, 2,6-dimethoxyphenyl, and 2-mesityl.

In some embodiments, the nickel pre-catalyst comprises at least one leaving group. In some embodiments, the nickel pre-catalyst comprises one leaving group. In some embodiments, the nickel pre-catalyst comprises two leaving groups. The term "leaving group" is given its ordinary meaning in the art and refers to an atom or a group capable of being displaced by a nucleophile. Non-limiting examples of suitable leaving groups include halides (e.g., chloride, bromide, and iodide), alkanesulfonyloxy, arenesulfonyloxy, alkyl-carbonyloxy (e.g., acetoxy), arylcarbonyloxy, mesyloxy, tosyloxy, trifluoromethane-sulfonyloxy, aryloxy (e.g., 2,4-dinitrophenoxy), methoxy, N,O-dimethylhydroxylamino, pixyl, and the like. In some embodiments, L is OSiR'₃, OH, Cl, Br, I, O-tosyl, O-mesyl, or OPO(OR')₂ wherein each R' is independently hydrogen, optionally substituted alkyl, optionally substituted heteroalkyl, optionally substituted aryl, or optionally substituted heteroaryl. In some cases, the at least one leaving group is selected from the group consisting of halide, o-tosyl, and o-mesyl. In some cases, the at least one leaving group is a halide. In some embodiments, the at least one leaving group is Cl. In some cases, the at least one leaving group is Br. In some cases, the at least one leaving group is O-tosyl. In some cases, the at least one leaving group is O-mesyl.

In some embodiments, the nickel pre-catalyst has the structure:

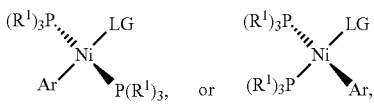

wherein each $R^1$ is independently optionally substituted alkyl, optionally substituted cycloalkyl, or optionally substituted aryl, or any two $R^1$ are optionally joined together to form a ring; Ar is the at least one aryl ligand, and LG is the at least one leaving group. In some embodiments, each $R^1$ is independently optionally substituted alkyl, optionally substituted cycloalkyl, or optionally substituted aryl. Each $R^1$ may be as described above in connection with the phosphine ligands, and/or each leaving group and aryl group are as described herein. In some embodiments, the pre-catalyst has the structure:

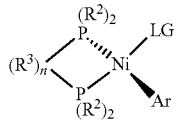

wherein each $R^2$ is independently optionally substituted alkyl, optionally substituted cycloalkyl, or optionally substituted aryl, or any two $R^2$ are joined together to form a ring; each $R^3$ is optionally substituted alkylene, optionally substituted heteroalkylene, optionally substituted arylene, optionally substituted heteroarylene, or optionally substituted ferrocenylene; n is 1, 2, 3, 4, 5, or 6; Ar is the at least one aryl ligand; and LG is the at least one leaving group. In some embodiments, each $R^2$ is independently optionally substituted alkyl, optionally substituted cycloalkyl, or optionally substituted aryl. Each $R^2$ and $R^3$ may be as described above in connection with the phosphine ligands, and/or each leaving group and aryl group are as described herein.

In some embodiments, the pre-catalyst has the structure:

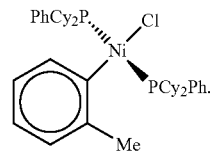

(trans-(PCy$_2$Ph)$_2$Ni(o-tolyl)Cl)

In other embodiments, the pre-catalyst is not:

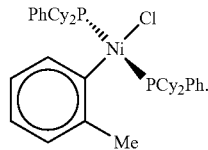

In some embodiments, the pre-catalyst is selected from the group consisting of a trans-(PPh$_3$)$_2$Ni(o-tolyl)Cl, trans-(PCyPh$_2$)$_2$Ni(o-tolyl)Cl, trans-(PCy$_2$Ph)$_2$Ni(o-tolyl)Cl, trans-(PCy$_3$)$_2$Ni(o-tolyl)Cl, trans-(PCyp3)$_2$Ni(o-tolyl)Cl, trans-(PBn$_3$)$_2$Ni(o-tolyl)Cl, trans-(PMe$_2$Ph)$_2$Ni(o-tolyl)Cl, trans-(PMe$_2$Ph)$_2$Ni(2,4,6-triisopropylphenyl)Br, trans-(PMe$_2$Ph)$_2$Ni(2,6-dimethoxyphenyl)Br, trans-(PEt$_3$)$_2$Ni(2-mesityl)Br, trans-(PnBu$_3$)$_2$Ni(2-mesityl)Br, cis-[dppe]Ni(o-tolyl)Cl, cis-[dppe]Ni(o-tolyl)Cl, cis-[dppp]Ni(2-mesityl)Br, trans-[dppb]Ni(2-mesityl)Br, cis-[(S)-BINAP]Ni(o-tolyl)Cl, cis-[dppf]Ni(o-tolyl)Cl, trans-[dcpf]Ni(o-tolyl)Cl, trans-[xantphos]Ni(o-tolyl)Cl, and cis-[pyphos]Ni(o-tolyl)Cl. In some embodiments, the pre-catalyst is selected from the group consisting of a trans-(PPh$_3$)$_2$Ni(o-tolyl)Cl, trans-(PCyPh$_2$)$_2$Ni(o-tolyl)Cl, trans-(PCy$_3$)$_2$Ni(o-tolyl)Cl, trans-(PCyp3)$_2$Ni(o-tolyl)Cl, trans-(PBn$_3$)$_2$Ni(o-tolyl)Cl, trans-(PMe$_2$Ph)$_2$Ni(o-tolyl)Cl, trans-(PMe$_2$Ph)$_2$Ni(2,4,6-triisopropylphenyl)Br, trans-(PMe$_2$Ph)$_2$Ni(2,6-dimethoxyphenyl)Br, trans-(PEt$_3$)$_2$Ni(2-mesityl)Br, trans-(PnBu$_3$)$_2$Ni(2-mesityl)Br, cis-[dppe]Ni(o-tolyl)Cl, cis-[dppe]Ni(o-tolyl)Cl, cis-[dppp]Ni(2-mesityl)Br, trans-[dppb]Ni(2-mesityl)Br, cis-[(S)-BINAP]Ni(o-tolyl)Cl, cis-[dppf]Ni(o-tolyl)Cl, trans-[dcpf]Ni(o-tolyl)Cl, trans-[xantphos]Ni(o-tolyl)Cl, and cis-[pyphos]Ni(o-tolyl)Cl.

The pre-catalysts described herein may be prepared using techniques known to those of ordinary skill in the art. In some embodiments, a pre-catalyst may be prepared by reacting a nickel source with a dative ligand (e.g., phosphine ligand, phosphite ligand, N-heterocyclic carbene, etc.), followed by reaction with a Grignard reagent or equivalent of the aryl ligand. For example, see FIG. 1 which illustrates non-limiting methods for forming pre-catalyst comprising monodentate or bidentate phosphine ligand(s). Non-limiting examples of nickel sources include Ni(OAc)$_2$, Ni(acac)$_2$, NiX$_2$ wherein X is a halide (e.g., NiCl$_2$, NiBr$_2$) optionally hydrated (e.g., NiX$_2$-6H$_2$O), (PPh$_3$)NiCl$_2$, Ni(PPh$_3$)$_4$, Ni(COD)$_2$, Ni(NO$_3$)$_2$, NiSO$_4$, Ni(ClO$_4$)$_2$, Ni(BF$_4$)$_2$, and Ni(OTf)$_2$. In some embodiments, the Ni source is not Ni(COD)$_2$. The reaction to form a catalyst may be carried out under any suitable conditions, for example, solvent, temperature, atmosphere, etc.

The pre-catalysts described herein may be activated using any suitable technique to form a catalyst. In some embodiments, the method of activating catalyst comprises exposing the pre-catalyst to an activating agent. The activating agent, for example, may be a nucleophilic reagent or an electrophilic reagent. Non-limiting examples of activating agents include R$_2$CuLi, RMgX, RZnX, R(R")$_2$B, R$_3$B, RL$_1$, R$_3$SiH, and R$_3$SiOTf, wherein each R is the same or different and is optionally substituted alkyl or optionally substituted aryl; each R" is optionally substituted alkyl, optionally substituted aryl, optionally substituted heteroalkyl, optionally substituted heteroaryl, or optionally substituted alkoxy, and X is a halide. In some cases, the activating agent is R$_3$SiOTf (e.g., Me$_3$SiOTf, Et$_3$SiOTf, etc.). In some cases, the activation may be conducted in the presence of oxygen as described herein. In some cases, the activating agent is a trialkyl borane, a boronic acid, a boronic ester, or a boroxine.

The activated pre-catalysts (e.g., catalysts) may be employed in a wide variety of organic reactions, as described herein. In some embodiments, methods of performing a nickel-catalyzed reaction are provided, wherein the reaction is performed in the presence of oxygen and a nickel catalyst. In some cases, the reaction is carried out at or below room temperature (e.g., at or below about 25° C.). Other suitable temperatures are described herein. In some cases, the nickel catalyst is formed by activation of a pre-catalyst as described herein.

A pre-catalyst may be activated prior to exposure to the reagents for the organic reaction or may be activated in situ. In some embodiments, the activation is carried out in the presence of the reactants for the organic reaction. That is, a reaction mixture may be formed comprising a pre-catalyst and reagents for an organic reaction, wherein the pre-catalyst is activated to form the corresponding catalyst in situ. As a specific non-limiting example, wherein the reaction comprises reaction of a benzyl chloride with a terminal alkene, a solution may be prepared comprising the benzyl chloride, the terminal alkene, and the pre-catalyst, wherein the pre-catalyst is activated via addition of an activating agent to the solution. Alternatively, the catalyst may be formed prior to exposure to the reagents. For example, the pre-catalyst may be activated via addition of an activating agent, followed by addition of the reactants (e.g., benzyl chloride and terminal alkene).

A catalyst (e.g., as part of a catalytic system) may be provided in any suitable amount for the reaction. In some embodiments, a catalyst is provided in about 1 mol %, about 2 mol %, about 3 mol %, about 4 mol %, about 5 mol %, about 6 mol %, about 7 mol %, about 8 mol %, about 9 mol %, about 10 mol %, or greater, versus the limiting reagent. In some embodiments, a catalyst is provided in an amount between about 1 mol % and about 10 mol %, or about 5 mol % and about 10 mol %, or about 5 mol % and about 15 mol %, versus the limiting reagent.

The catalysis may be carried out under any suitable conditions. Those of ordinary skill in the art will be able to use the guidelines described herein to select appropriate reaction conditions for the selected reactant without undo experimentations. Non-limiting parameters which may be varied include the solvent selection, the temperature of reaction, the nature of the substituents on the reactant, the amount of catalyst, and/or the reaction time. In some cases, the reaction is carried out at about room temperature. The reaction may be carried out for any suitable period of time. In some cases, the reaction is carried out until the reaction is about 50%, about 60%, about 70%, about 80%, about 90%, about 93%, about 95%, about 96%, about 97%, about 98%, about 99%, about 99.5%, or greater, complete. That is, the reaction is carried out for a period of time until a selected percent of the starting material has been converted into a product. In some cases, the reaction is greater than about 50%, about 60%, about 70%, about 80%, about 90%, about 93%, about 95%, about 96%, about 97%, about 98%, about 99%, about 99.5%, or greater, complete in a period of time of less than about 24 hours, less than about 12 hours, less than about 8 hours, less than about 6 hours, less than about 5 hours, less than about 4 hours, less than about 3 hours, less than about 2 hours, less that about 1 hour, less than about 50 minutes, less than about 40 minutes, less than about 30 minutes, or less.

In some cases, the reaction comprises reacting an optionally substituted benzyl chloride with a terminal alkene in the presence of the catalyst (e.g. formed in an activation of a pre-catalyst, as described herein). In some cases, the reaction is stereoselective via reaction of the external position of the terminal alkene. In other cases, the reaction is stereoselective via reaction of the internal position of the terminal alkene. In some embodiments, the ratio of the product formed via reaction of the internal position of the terminal alkene to the external position of the terminal alkene is greater than or equal to about 99:1, or about 98:2, or about 97:3, or about 95:5, or about 93:7, or about 90:10. The terminal alkene and benzyl chloride may be provided in any suitable ratio, for example about 10:1, or about 8:1, or about 5:1, or about 4:1, or about 3:1, or about 2:1, or about 1:1, or between about 10:1 and about 1:1, or between about 7:1 and about 3:1, or between about 5:1 and about 1:1. In some cases, the terminal alkene is provided in excess with respect to the benzyl chloride.

In some embodiments, the benzyl chloride has the structure:

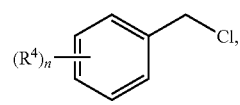

wherein each $R^4$ is independently halo, optionally substituted alkyl, optionally substituted heteroalkyl, optionally substituted alkylene, optionally substituted aryl, optionally substituted —O-alkyl, —SO$_2$-alkyl, —COOH, —COO-alkyl, or any two $R^4$ can be joined together to form a ring; and n is 0, 1, 2, 3, 4, or 5. In some embodiments, the ortho position of the benzyl chloride is not substituted. In some embodiments, the ortho position(s) of the benzyl chloride does not comprise an ester group. In some embodiments, the benzyl chloride does not comprise any groups which are reactive with the activating agent. In some embodiments, the reaction is carried out in the presence of an amine (e.g., NEt$_3$, NEt($^i$Pr)$_2$, etc.).

In some embodiments, the terminal alkene has the structure:

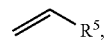

wherein $R^5$ is optionally substituted alkyl, optionally substituted cycloalkyl, optionally substituted alkylene, optionally substituted heteroalkyl, optionally substituted alkyl-aryl, or optionally substituted aryl. In some embodiments, the alkene does not comprise any groups which are reactive with the activating agent.

In some embodiments, the product of the reaction between the optionally substituted benzyl chloride and the terminal alkene is:

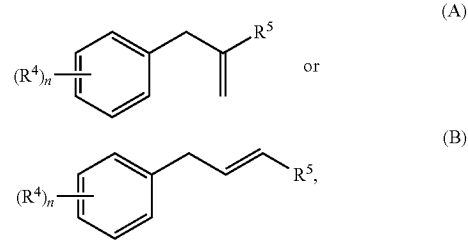

wherein $R^4$ and $R^5$ are as described above for the benzyl chloride and the terminal alkene, respectively. In some embodiments, the ratio of product (A):(B) is greater than or equal to about 99:1, or about 98:2, or about 97:3, or about 95:5, or about 93:7, or about 90:10. In some embodiments, the product of the reaction between the optionally substituted benzyl chloride with a terminal alkene is:

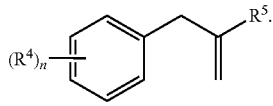

In other embodiments, the product of the reaction between the optionally substituted benzyl chloride with a terminal alkene is:

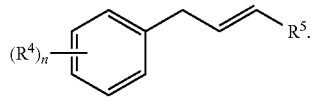

Figure 2:
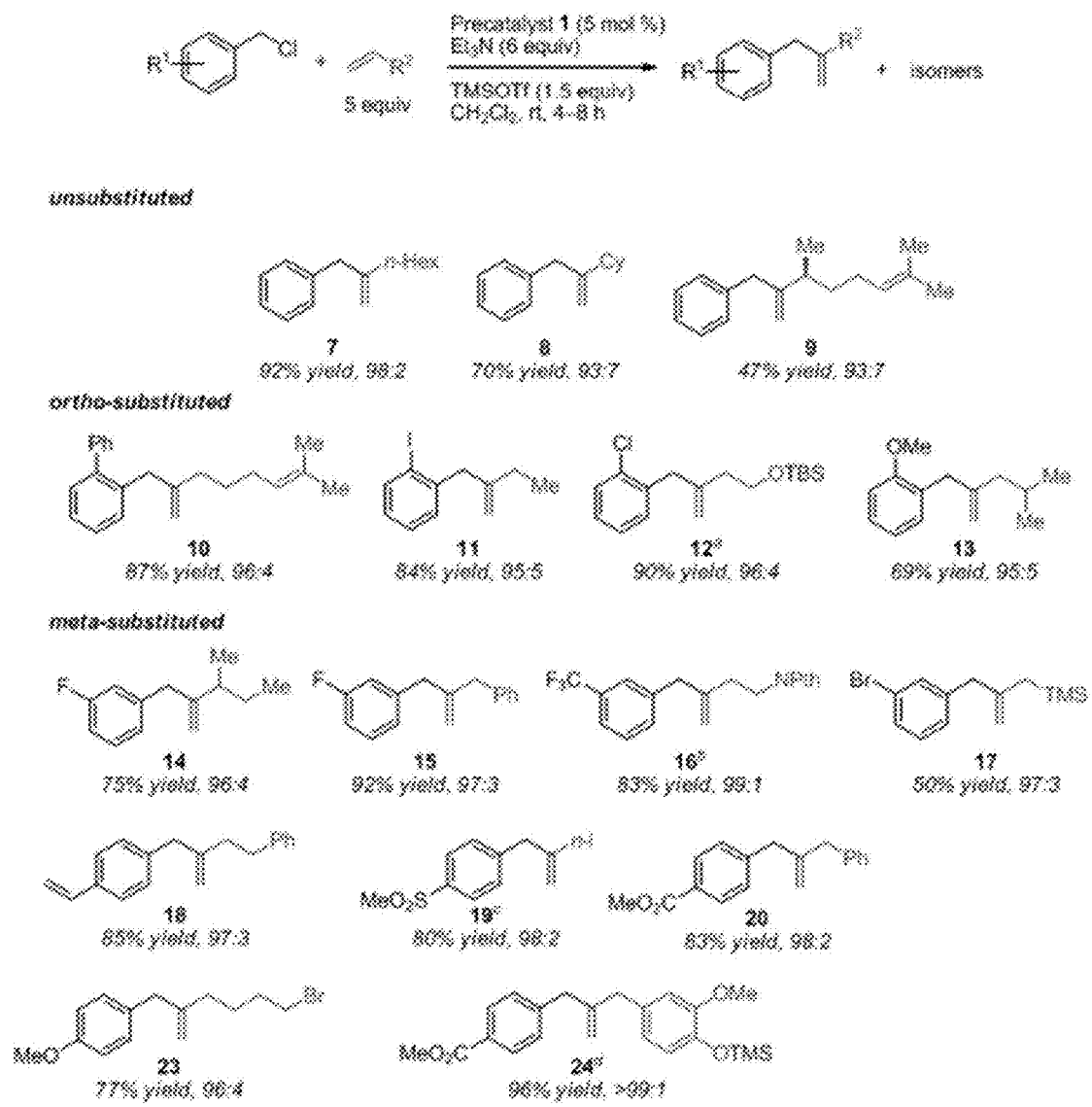
FIG. 2 shows non-limiting products form via reaction of a benzyl chloride and a terminal alkene in the presence of a catalyst, according to some embodiments.
Figure 2:
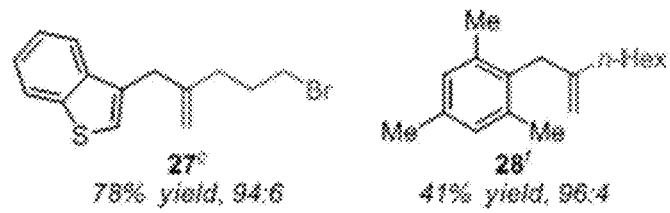
Figure 2:
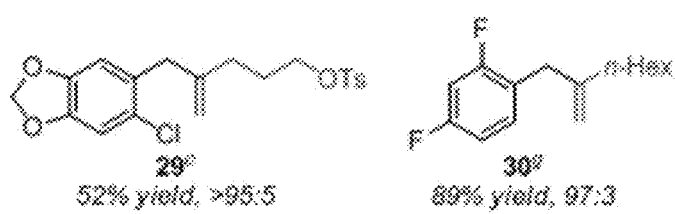
Figure 2:
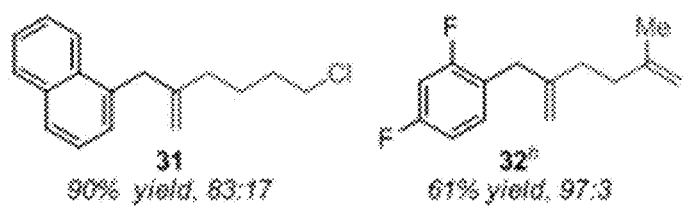
Figure 2:
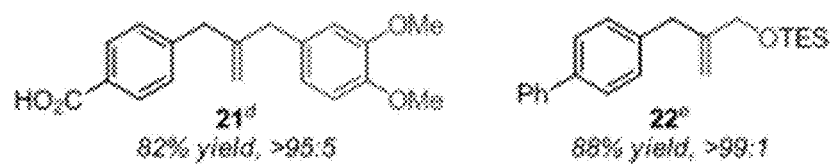
Figure 2:
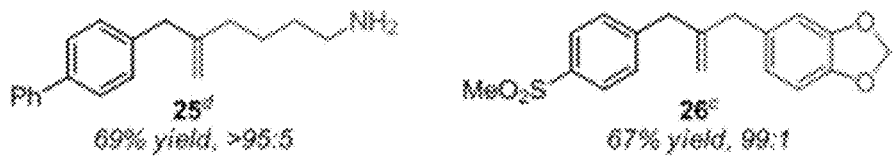

In some embodiments, the product of the reaction is as given in FIG. 2.

In other embodiments, the reaction comprises reacting a terminal alkene with an aldehyde and a silyl triflate in the presence of a catalyst (e.g. formed via activation of a pre-catalyst, as described herein). The terminal alkene may have a structure as described above. In some embodiments, the aldehyde has the structure $HC(=O)R^6$, wherein $R^6$ is optionally substituted alkyl or optionally substituted aryl. In some embodiments, the silyl triflate has the structure $(R^7)_3SiOTf$, wherein each $R^7$ is the same or different and is optionally substituted alkyl or optionally substituted aryl.

Those of ordinary skill in the art will be able to utilize the pre-catalysts and catalysts described herein in a number of catalytic transformations, for example, see those disclosed in Ho et al., *Highly Selective Coupling of Alkenes and Aldehydes Catalyzed by [Ni(NHC){P(OPh)₃}]: Synergy between a Strong s Donor and a Strong π Acceptor*, Angew. Chem. Int. Ed., Vol. 46, 2007, pp. 782-785; Ho et al., *α-Olefins as Alkenylmetal Equivalents in Catalytic Conjugate Addition Reactions*, Angew. Chem. Int. Ed., Vol. 47, 2008, pp. 1893-1895; Ng et al., *Highly Enantioselective and Regioselective Nickel-Catalyzed Coupling of Allenes, Aldehydes, and Silanes*, J. Am. Chem. Soc., Vol. 127, 2005, pp. 7320-7321; Ng et al., *Nickel-catalyzed coupling of terminal allenes, aldehydes, and silanes*, Tetrahedron, Vol. 62, 2006, pp. 11350-11359; Molinaro et al., *Nickel-Catalyzed Reductive Coupling of Alkynes and Epoxides*, J. Am. Chem. Soc., Vol. 125, 2003, pp. 8076-8077; Patel et al., *Asymmetric Catalytic Coupling of Organoboranes, Alkynes, and Imines with a Removable (Trialkylsilyloxy)ethyl Group—Direct Access to Enantiomerically Pure Primary Allylic Amines*, Angew. Chem. Int. Ed., Vol. 43, 2004, pp. 3941-3944; and Matsubara et al., *Nickel-Catalyzed Allylic Substitution of Simple Alkenes*, J. Am. Chem. Soc., Vol. 132, 2010, pp. 6880-6881; each incorporated herein by reference.

In some embodiments, the reactions (e.g. activation, catalysis) described herein may be carried out in the presence of oxygen. For example, a reaction may be carried out using conditions that do not specifically exclude the presence of oxygen, for example, in reagents or solvents. In some cases, the reaction is carried out without degassing and/or drying the solvents and/or reagents employed in the reaction.

The methods described herein may be carried out at any suitable temperature. In some cases, the methods are carried out at or about room temperature (e.g., about 25° C.). In some cases, the methods are carried out at room temperature or below (e.g., less than or equal to about 25° C.). In other cases, the methods are carried out at room temperature or above (e.g., greater than or equal to about 25° C.).

The methods described herein may be carried out in any suitable solvent, including, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane), and alcohol solvents (e.g., ethanol, methanol, propanol, isopropanol, tert-butanol). Non-limiting examples of solvents useful include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine. In some embodiments, the solvent is dichloromethane. In some embodiments, the solvent is toluene.

Definitions

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively. In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly (ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl;

heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituets recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl) aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from the group consisting of fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary ($-NH_2$), secondary ($-NHR_x$), tertiary ($-NR_xR_y$), or quaternary ($-N^+R_xR_yR_z$) amine, where $R_x$, $R_y$, and $R_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

These and other aspects of the present invention will be further appreciated upon consideration of the following Examples, which are intended to illustrate certain particular embodiments of the invention but are not intended to limit its scope, as defined by the claims.

EXAMPLE 1

Figure 3:
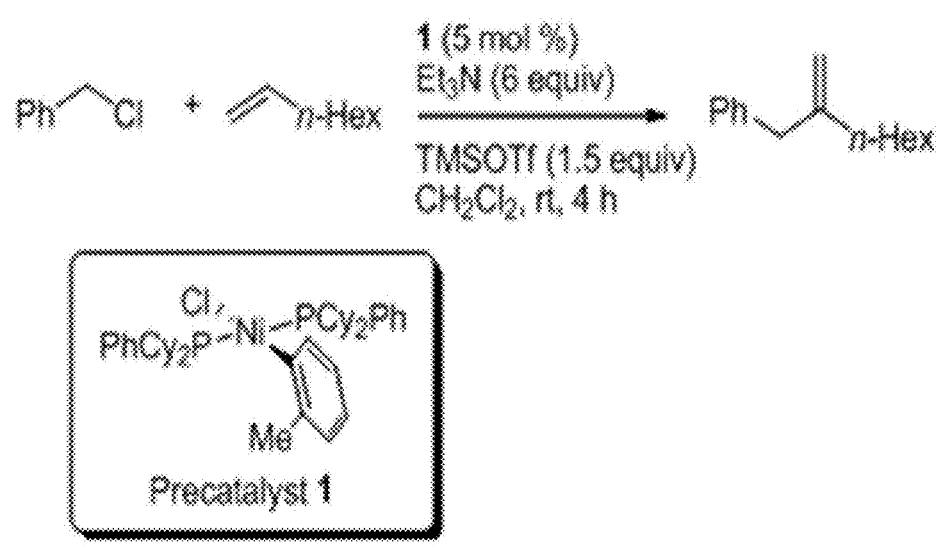
FIG. 3 illustrates a non-limiting organic reaction employing a catalyst formed from a pre-catalyst, according to some embodiments.

In this example, the preparation and use of an air-stable nickel precatalyst for internally-selective Heck reactions of terminal, electronically unbiased alkenes and benzyl chlorides is described (FIG. 3). The reaction proceeds at room temperature to provide 1,1-disubstituted alkenes and no exclusion of air or moisture is required during the setup of each reaction, nor is drying, degassing, or purification of any reagents required, in stark contrast to what is typically required for nickel(0) catalyzed reactions.

Results and Discussion

During early investigations of this reaction, catalysts comprising the combination of Ni(COD)$_2$ and PCy$_2$Ph effected benzylation of the COD ligands themselves in preference to the intended alkene substrate in some instances. This observation led us to hypothesize that COD was coordinating to nickel with greater affinity than the intended alkene, effectively acting as a competitive inhibitor, causing a rate reduction of the desired transformation. Thus, removing COD from the reaction could allow for a greater turnover frequency and/or a reduced catalyst loading, and potentially allow for the use of more sterically hindered alkenes or even disubstituted alkenes as viable substrates. A nickel (0) precatalyst was synthesized to test this hypothesis (Scheme 1).

Scheme 1. Synthesis of $(PCy_2Ph)_2Ni(\eta^2\text{-}C_2H_4)$

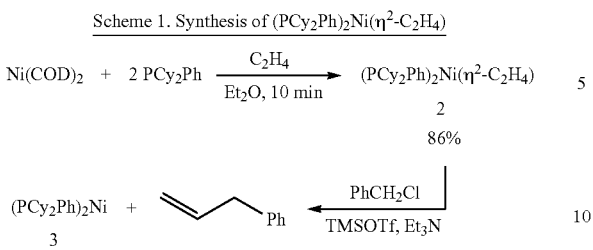

Complex 3 was not isolated; its yield was determined indirectly to be >98% based on the amount of allylbenzene formed (measured by GC).

Treatment of complex 2 with benzyl chloride, $Et_3N$, and TESOTf facilitated the benzylation of ethylene to yield allylbenzene and $(PCy_2Ph)_2Ni(0)$ (3), which is believed to be the catalytically active species. Even at half the catalyst loading (5 mol % instead of 10 mol % employed previously), the coupling of benzyl chloride with 1-octene proceeds faster than when $Ni(COD)_2$ and $PCy_2Ph$ are used as the catalyst. Furthermore, addition of COD to a reaction catalyzed by 2 retards the rate relative to a control experiment in which no COD was added. Thus, the presence of COD decreased the rate of this coupling reaction.

These results provide the evidence showing the COD ligands in $Ni(COD)_2$ are not innocent in a reaction such as this coupling.

Though precatalyst 2 had proven interesting and had provided valuable information regarding the role of COD in the reaction, it required inert-atmosphere techniques for its synthesis, storage, and usage. As such, other possible precatalysts that would possess the same properties, but also tolerate storage under air were developed.

The synthesis of the complex trans-$(PCy_2Ph)_2Ni(o\text{-tolyl})Cl$ (1) was completed and determined that it can be conveniently synthesized in a two-step procedure beginning from $NiCl_2 \cdot 6H_2O$ and $PCy_2Ph$, followed by addition of one equivalent of o-tolylmagnesium chloride to yield 1 as a yellow, diamagnetic, air-stable solid (Scheme 2). Alternatively, the ligand $PCy_2Ph$ can be easily synthesized from dichlorophenylphosphine and cyclohexylmagnesium chloride, which can either be made from chlorocyclohexane or purchased commercially. No purification steps were required in this sequence, making the synthesis of precatalyst 1 remarkably convenient.

Scheme 2. Synthesis of trans-$(PCy_2PH)_2Ni(o\text{-tolyl})Cl$

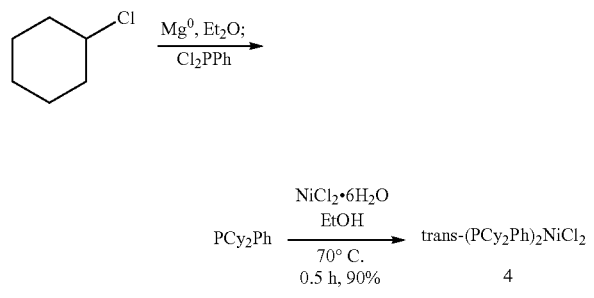

-continued

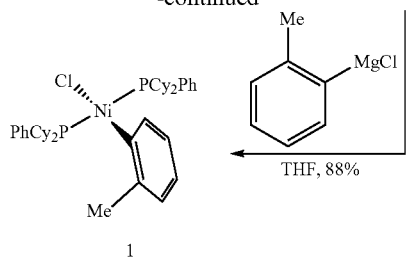

Figure 4:
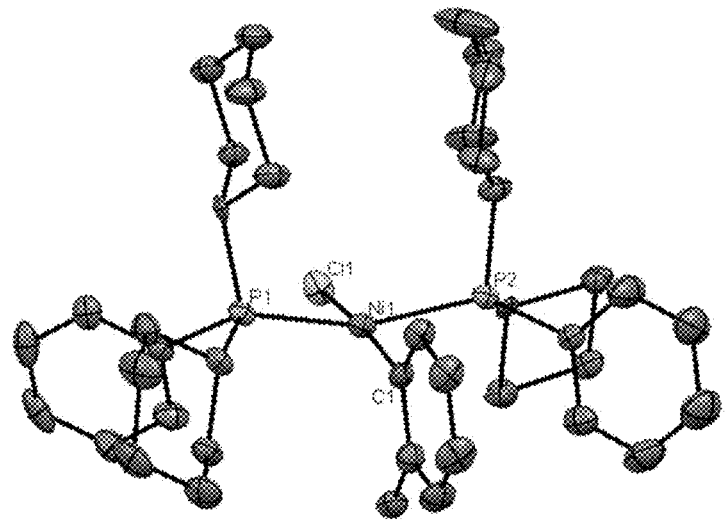
FIGS. 4 and 6 shows the x-ray crystal structures of number of pre-catalysts, according to some embodiments.
Figure 4:
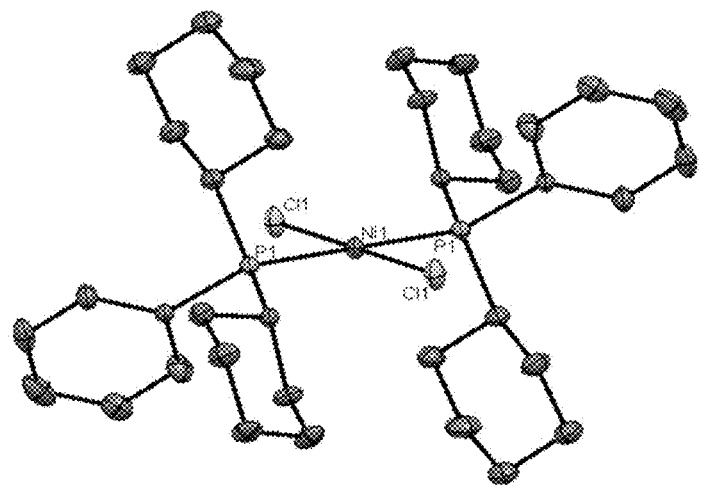

Precatalyst 1 as well as the intermediate complex trans-$(PCy_2Ph)_2NiCl_2$ (4) were characterized by single-crystal X-ray diffraction (see thermal ellipsoid representations in FIG. 4); 4 adopts a nearly ideal square planar geometry with trans stereochemistry. This complex is diamagnetic and air-stable, and can be stored exposed to air at room temperature indefinitely. Likewise, complex 1 assumes a trans stereochemistry and square planar geometry, and is stable towards air. The geometry of 4 is somewhat distorted toward a tetrahedral arrangement, as indicated by the observed P—Ni—P bond angle of 161.7° and Cl—Ni—C bond angle of 170.4°, both noticeably shy of the ideal 180°. In FIG. 4: Thermal ellipsoid representations of trans-$(PCy_2Ph)_2Ni(o\text{-tolyl})Cl$ (1, top) and trans-$(PCy_2Ph)_2NiCl_2$ (4, bottom) with ellipsoids at 50% probability level. Hydrogen atoms and disorder on ligands not shown for clarity.

Upon treatment of complex 1 with an alkene, silyl triflate, and base, reduction from the Ni(II) precatalyst to the catalytically-active Ni(0) species occurs within minutes at room temperature. This could occur by arylation of the alkene as illustrated in Scheme 3; however, 2,2'-dimethylbiphenyl (6, 97% yield by GC) was formed rather than styrene 5. Indeed, treatment of the precatalyst with TMSOTf effects reduction to a nickel(0) species and 6 even in the complete absence of any alkene. This suggests that, following chloride abstraction from 1, transmetallation with another molecule of 1 to produce 1a and 1b occurred. Subsequently, reductive elimination of 6 from complex 1a is likely the means by which production of nickel(0) takes place. This in turn suggests that only half of the precatalyst is ultimately reduced—presumably the other half is converted to the catalytically-inactive $(PCy_2Ph)_2Ni(Cl)(OTf)$ (1b), unless reduction of 1b through another mechanism is concurrently active.

Entry into a nickel(0) manifold from nickel(II) promoted by an additive such as a silyl triflate is unprecedented. In the vast majority of cases, reduction of a nickel(II) species to the catalytically active form is effected in one of 4 ways: (1) by consumption of an organometallic reactant present in the reaction, such as a boronic acid; (2) by an exogenous reductant such as zinc, manganese, or sodium-mercury amalgam, which is added to carry out the reduction by electron transfer; (3) by addition of an organometallic reagent such as $AlMe_3$, $Et_2Zn$, or MeMgBr, which can effect reduction through two successive transmetallations to yield a dialkylnickel(II) complex, which undergoes reductive elimination to yield an alkane and a nickel(0) species; or (4) by addition of a hydride donor such as DIBAL, methanol, or isopropanol. The ability to enter into a nickel(0) catalytic cycle at room temperature and without the use of pyrophoric or strongly basic reagents represents a new and potentially valuable means of entry into nickel(0) species which could be employed for a wide variety of nickel(0)-catalyzed reactions.

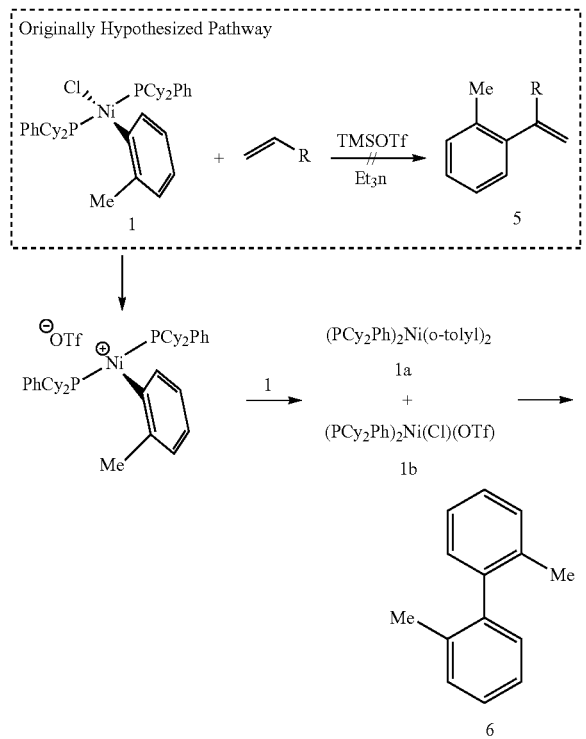

Scheme 3. Activation of Precatalyst 1

Having established the competence of precatalyst 1 for this coupling reaction, the reaction was optimized, ultimately arriving at the conditions described in Table 1, with the conditions in entry 4 being chosen to utilize in additional reactions. The was investigated reaction under solvent-free (neat) conditions, and it was observed that these conditions performed quite poorly. This may be attributed to the low solubility of precatalyst 1 in triethylamine, which causes very slow activation. However, even in toluene, activation of the precatalyst is not facile, as entry 2 highlights: even after 1 hour, only 2% of product has been produced, and although the reaction ultimately does reach completion, it requires nearly 24 hours to do so. The addition of COD to the reaction mixture was shown to again reduce the rate of reaction (entry 3).

Changing the reaction solvent to dichloromethane facilitated rapid activation of the catalyst and a greatly accelerated coupling, requiring only 4 hours for the reaction to reach complete conversion (cf. entries 2 and 4), which corresponds approximately to a five-fold rate enhancement. The change from toluene to $CH_2Cl_2$ also allowed for a reduction of the excess of alkene required (cf. entries 4-9). In toluene, changing from 5 to 2 equiv of alkene caused a marked decrease in the yield, even after 24 hours of reaction time (92% vs. 54%). However, in $CH_2Cl_2$, changing from 5 to 2 equiv of alkene ultimately afforded the product in only a slightly diminished yield (96 vs. 84%), though the reaction rate was decreased. As the excess further decreases, however, the yield begins to drop considerably, ultimately to 68% when a 1:1 stoichiometry of benzyl chloride and alkene was used.

Also interesting is the marked reduction in yield observed when Hünig's Base ($Et^iPr_2N$) is used instead of triethylamine (cf. entries 4 and 11). Though of similar thermodynamic basicity, this likely suggests that the sterically less hindered $Et_3N$ is capable of deprotonating the nickel hydride (formed after β-hydride elimination—FIG. 5, vide infra) much more efficiently.

Prior to beginning this optimization process, one of the changes investigated was whether the use of dried and degassed solvents and reagents is necessary to obtain satisfactory results. Preliminary trials showed that using reagents and solvents "as received" had no negative effects on the yield of the reaction, however a direct comparison was carried out to rigorously verify this observation. As the comparison between entries 4 and 12 indicates, the reaction does appear to proceed more rapidly when purified and degassed reagents are employed, but ultimately the same yield is achieved in both cases. This difference in rate may be attributed to the oxygen mediated decomposition of some portion of the catalyst when unpurified reagents are employed, causing the effective catalyst loading to be slightly less than the nominal loading. Having verified the absence of negative effects, all further reactions were carried out without purification or degassing of any reagents, taking the conditions described in entry 4 as the optimized conditions.

Having satisfactorily optimized the conditions for the coupling reaction, the scope of the reaction were examined, the results of which are shown in FIG. 2. In FIG. 2: Yields listed are isolated yields. Ratios reported represent the ratio of the major (branched) product to the sum of all other isomers as determined by GC. Ratios reported as >95:5 were determined by NMR. [a]TBSOTf and 3 equiv 3-buten-1-ol used in place of TMSOTf. [b]3 equiv alkene used. [c]TESOTf used in place of TMSOTf. [d]Excess TMSOTf used to effect in situ protection. [e]TESOTf and 3 equiv allyl alcohol used in place of TMSOTf. [f]Ratio was 78:22 prior to purification. The linear and branched products were separable by column chromatography. [g]Reaction carried out on 10 mmol scale. [h]Product contained an inseparable byproduct (ca. 10% by mass) formed by the oligomerization of 2-methyl-1,5-hexadiene.

TABLE 1

Optimization of reaction parameters

| | | % Yield at time (h) | | |
|---|---|---|---|---|
| entry | Change from above conditions | 1 | 3 | 24 |
| 1 | Neat | 1 | 3 | 11 |
| 2 | PhMe | 2 | 40 | 92 |
| 3 | PhMe, 10 mol % 1,5-COD added | 2 | 16 | 76 |
| 4 | $CH_2Cl_2$ | 51 | 68 | 96 |
| 5 | $CH_2Cl_2$, 2 equiv 1-octene | 35 | 52 | 84 |
| 6 | $CH_2Cl_2$, 1.3 equiv 1-octene | 21 | 40 | 79 |
| 7 | $CH_2Cl_2$, 1 equiv 1-octene | 19 | 38 | 68 |
| 8 | PhMe, 3.5 equiv 1-octene | 1 | 11 | 73 |
| 9 | PhMe, 2 equiv 1-octene | 1 | 8 | 54 |
| 10 | $CH_2Cl_2$, TESOTf inst. TMSOTf | 48 | 65 | 95 |
| 11 | $CH_2Cl_2$, $Et^iPr_2N$ instead of $Et_3N$ | 2 | 6 | 12 |
| 12 | Purified and degassed reagents[a] | 59 | 76 | 95 |

In Table 1: All yields were determined by gas chromatography against a calibrated internal standard. All reagents were used "as received" except where explicitly stated. Many reactions were complete prior to 24 hours, but were run for the full 24 hours for comparison purposes. [a] liquid reagents and solvents were dried over a suitable drying agent and distilled, followed by three cycles of freeze-pump-thaw degassing.

The reaction was highly selective for the branched product over the linear product across a wide variety of electronically and sterically differentiated benzyl chlorides and alkenes. The selectivity, described by the ratio between the branched product and the sum of all other isomers observed, was greater than 95:5 in nearly all instances, which not only indicates an intrinsically high selectivity for the branched product over the linear product, but it also shows that isomerization of the product after its formation is extremely minimal. Substitution in the ortho, meta, and para positions of the benzyl chloride was well tolerated, including fluorine, chlorine, bromine, and iodine substituents (ex. 11, 12, 14, 15, 17). Some addition of nickel into the C—I bond was observed, but the yield of the corresponding desired product (11) was not significantly diminished. The tolerance of aryl halides is significant since this enables the construction of halogen-substituted allylbenzene derivatives, which can then be directly used in further cross-coupling reactions, if desired. Oxidative addition of Ni(0) phosphine complexes into aryl fluorides, chlorides, bromides, and iodides is well established, so the excellent chemoselectivity of the oxidative addition into the benzyl $sp^3C$—Cl bond in preference to the $sp^2C$—X bonds suggests the former occurs significantly faster than the latter.

As examples 23, 27, 29, and 31 demonstrate, primary alkyl chlorides, bromides, and tosylates were tolerated—again, this speaks to the excellent chemoselectivity of the oxidative addition into the benzyl $sp^3C$—Cl bond in preference to primary $sp^3C$—Cl, $sp^3C$—Br, and $sp^3C$—OTs bonds. Construction of these 1° alkyl electrophiles could prove useful, whether it be for nucleophilic substitution reactions, cross couplings, or in the preparation of nucleophilic organometallic reagents such as Grignard, organolithium, or organozinc reagents.

Additionally, the use of alternative silyl triflate additives were investigated. In the majority of cases, TMSOTf could be used in place of the more expensive TESOTf with no detrimental effects, though there are some instances in which the greater Lewis acidity of TMSOTf compared to that of TESOTf causes partial decomposition of substrates. Likewise, TBSOTf is also a competent silyl triflate additive for this reaction.

Using these three different silyl triflate additives, in situ protection of free alcohols, carboxylic acids, and amines was possible on both the alkene and benzyl chloride coupling partners, directly yielding protected alcohols (12, 22), phenols (24), and following aqueous workup, free carboxylic acids (21) and amines (25). As illustrated by example 17, allyltrimethylsilane was a competent alkene coupling partner, though some protiodesilylation does occur (ca. 15%). In this particular example, the protiodesilylated material was separable by column chromatography, allowing clean isolation of 17, though in modest yield.

Styrenes were less reactive compared to α-olefins, as evidenced by the formation of 18 in high yield from 4-vinylbenzyl chloride and 3-butenylbenzene with no observable reaction at the styrene. Sulfur-containing functional groups, such as sulfones (19, 26) and benzothiophene (27) were tolerated with no apparent poisoning of the catalyst. Lastly, methylene acetals (26, 29) were compatible with the reaction conditions.

While most reactions proceed in good to excellent yield, a reduction in yield was observed from substitution on the ortho positions of the benzyl chloride or substitution adjacent to the olefin. Additionally, there were a few substrates which had reduced yield (scheme 4).

Scheme 4.

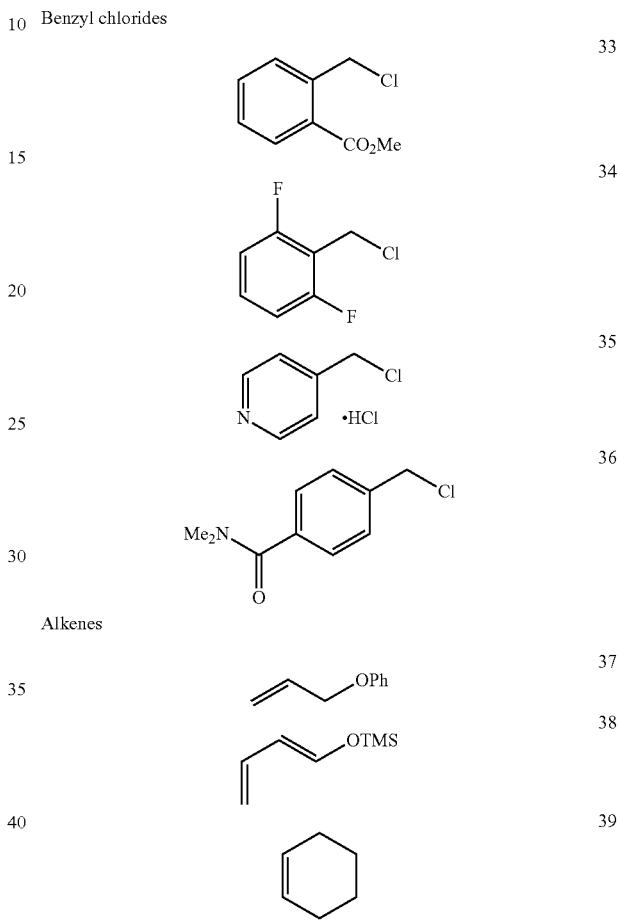

An ester moiety at the ortho position appeared to reduce or prevent catalytic turnover. Substitution of both the 2- and 6-positions of the benzyl chloride with fluorine (34) reduced or prevented product formation, leading to formation of the homocoupled product 1,2-bis(2,6-difluorophenyl)ethane. Additionally, 4-(chloromethyl)pyridine (34, as the HCl salt) provided little or no product. Finally, 4-(chloromethyl)-N,N-dimethylbenzamide (36) provided little or no product.

A number of alkenes also provided little or no product; allyl phenyl ether (37) underwent coupling, but also reacts with TESOTf, as does the coupling product, both of which decomposed to a significant extent. Diene 38 decomposed under the reaction conditions, and the rate of reaction of cyclohexene (39) was extremely low, with only traces of product formed, even after 48 hours of reaction time.

The profound selectivity for reaction with terminal, electronically unbiased alkenes in preference to styrenes (as evidenced by example 18) was investigated further. As shown in Scheme 5, the reaction between benzyl chloride and 1-octene proceeded in high yield; the analogous reaction with styrene, however, provided 40 in only 8% yield. The regiochemical outcome of the reaction with styrene: though not as selective as with aliphatic alkenes, substitution at the internal position was favored in a 78:22 ratio.

Scheme 5. Comparison of Styrene and α-olefins

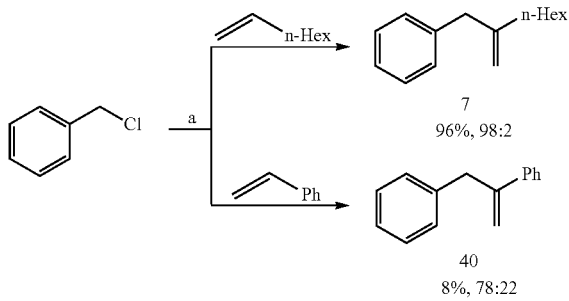

*Reaction conditions: precatalyst 1 (5 mol %), 5 equiv alkene (1-octene or styrene), Et3N (6 equiv), TMSOTf (1.5 equiv), 2 M in CH2Cl2. Yields and ratios determined by GC.

Figure 5:
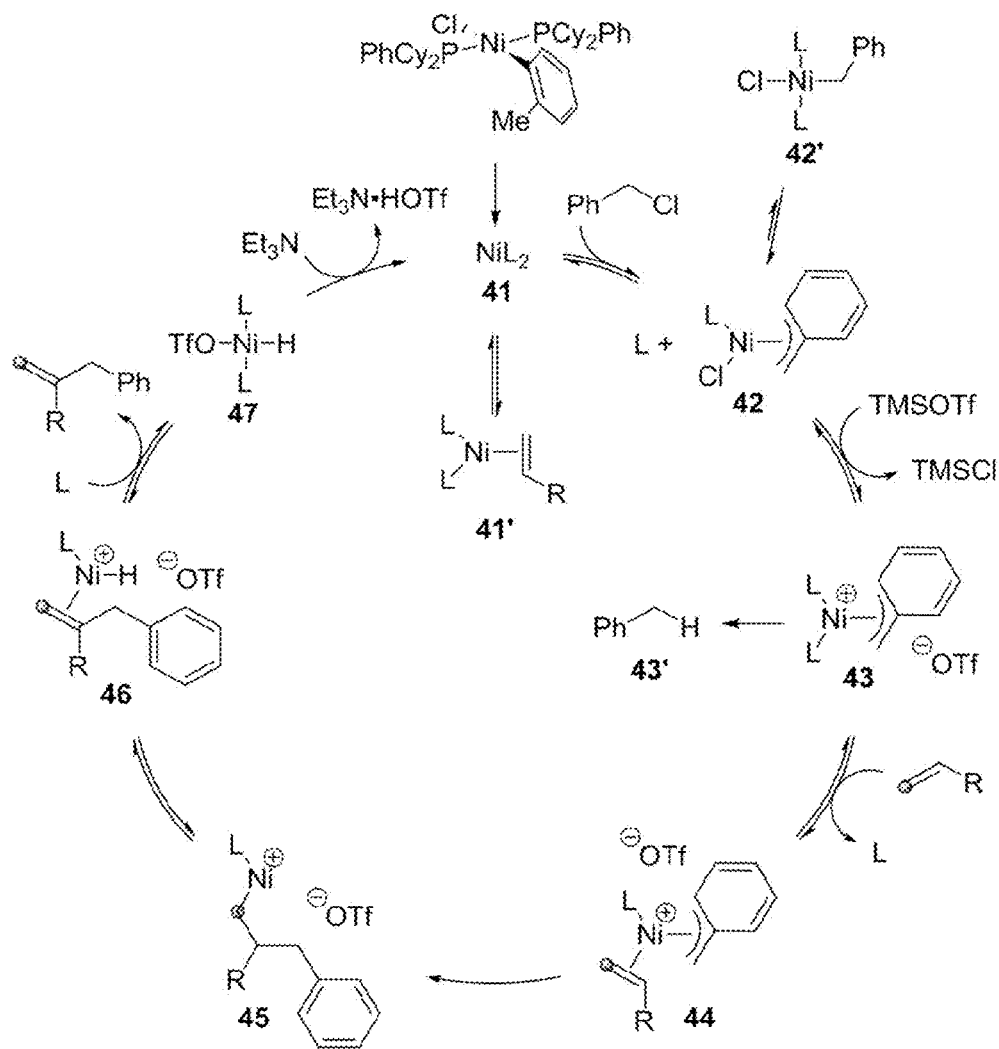
FIG. 5 illustrates an exemplary catalytic cycle, according to some embodiments.

During NMR spectroscopic characterization of complex 1, dissolution in CD2Cl2 caused was observed and the solution to take on a markedly red color compared to the pure yellow color observed in benzene. This difference is also reflected in the NMR spectra of the complex in C6D6 compared to CD2Cl2: the 31P NMR spectrum in C6D6 shows only a single peak at 16.1 ppm, whereas the spectrum in CD2Cl2 shows three signals—one at 15.0 ppm, corresponding to 1, as well as a signal at 3.1 ppm for free PCy2Ph and one downfield signal at 44.9 ppm, presumably (PCy2Ph)Ni(o-tolyl)Cl or a CD2Cl2 adduct thereof. On this basis, it is reasonable to suggest that dichloromethane may promote or stabilize dissociation of one PCy2Ph ligand, which may occur during the course of the reaction to allow coupling to occur, as outlined in the proposed mechanism (FIG. 5).

The proposed mechanism begins with reduction of the precatalyst 1 to the NiL2 species 41 (via the mechanism presented in Scheme 3), followed by rapid oxidative addition to yield 42, which is in equilibrium with 42'. Abstraction of chloride by the silyl triflate yields cationic nickel species 43, which facilitates alkene coordination to yield 44. This species undergoes f3-migratory insertion with the indicated regiochemistry to produce 45, with nickel bonded to the less substituted of the two carbons comprising the alkene. The migratory insertion step is likely irreversible, and it also determines the regiochemical outcome of the reaction: insertion as shown (44 to 45) provides the branched (desired) product, whereas insertion with the opposite regiochemistry will lead to formation of the linear product. Migratory insertion (44 to 45) occurs to form the new nickel-carbon bond to the less substituted carbon of the alkene, which is marked with o for emphasis. Following migratory insertion, β-hydride elimination to form nickel hydride 46 takes place. Product release, ligand association, and deprotonation by Et3N complete the catalytic cycle. One commonly observed side product (43'), formed by the formal protonation of benzyl nickel species 43, is often produced in small quantities during the course of the reaction. As the concentration of alkene decreases, the equilibrium between 43 and 44 shifts more toward 43, which results in a higher concentration of 43 at any given time, causing reduction product 43' to be formed in greater amounts. This may be the root cause for the decrease in yield observed as the amount of alkene used in the reaction is reduced or when more sterically hindered alkenes are used.

The principal factor for formation of the branched product in preference to the linear product may be the steric differentiation of the two ends of the alkene, which manifests itself as a difference in energy between the incipient 1° C—Ni and 2° C—Ni bond formed during migratory insertion (44 to 45). The less hindered 1° C—Ni bond is lower in energy, and as such, the transition state leading to its formation is also lower in energy. The uniformly high selectivity observed across a range of electronically diverse substrates supports this hypothesis, suggesting that electronic factors are of secondary importance in determining the regiochemical outcome of the migratory insertion, and thus of the reaction. The comparison between styrene and an aliphatic olefin (Scheme 5) further supports this hypothesis: while the branched product is still the major product, the selectivity is indeed reduced compared to electronically unbiased alkenes.

In summary, a convenient protocol for the internally-selective benzylation of terminal alkenes using the air-stable precatalyst trans-(PCy2Ph)2Ni(o-tolyl)Cl (1) was developed. This precatalyst is easily prepared from commercially available NiCl2 · 6H2O, PCy2Ph, and o-tolylmagnesium chloride in a high-yielding, two-step procedure, and can be stored open to air at room temperature with no measurable loss of purity or activity. Furthermore, all reagents used in the reaction can be used "as received" with no purification or even any degassing necessary. The reaction is tolerant of substitution on both the benzyl chloride and alkene coupling partners, allowing rapid access to a wide variety of substituted allylbenzene derivatives. Additionally, this study has provided useful information regarding the commonly employed nickel (0) source Ni(COD)2, demonstrating that the COD ligands are not innocent under all circumstances.

EXPERIMENTAL DATA

Section I. Materials, Methods, and General Considerations

For couplings catalyzed by trans-(PCy2Ph)2Ni(o-tolyl)Cl (1), no precaution to exclude air or water was taken, non-dried glassware was employed, and all reagents and solvents were used as received. For reactions requiring dry and/or oxygen-free conditions, tetrahydrofuran, toluene, dichloromethane, triethylamine, diethyl ether, benzene, and acetonitrile were degassed by sparging with nitrogen and dried by passage through a column of activated alumna on an SG Water solvent purification system. Manipulation of all air-sensitive reagents was carried out in a glovebox (MBraun Unilab) filled with dry nitrogen. Couplings using (PCy2Ph)2Ni(η2-C2H4) (2) required the exclusion of oxygen, so all liquid reagents were degassed by three freeze-pump-thaw cycles. Liquid alkenes were distilled from sodium metal, CaH2 or 4 Å molecular sieves as appropriate. Thin-layer chromatography was carried out on EMD Millipore 60 F254 glass-backed plates (silica gel, 250 μm coating thickness) and spots were visualized using UV light, basic potassium permanganate, ethanolic phosphomolybdic acid (PMA), or ceric ammonium nitrate (CAN) stains. Column chromatography was carried out on a Biotage Isolera chromatography system using SNAP KP-Sil columns (silica gel, 50 μm average particle size). Bis(1,5-cyclooctadiene)nickel(0) was purchased from Strem Chemicals (Newburyport, Mass.) and stored at −30° C. in a glovebox. Ethylene and 1-butene were purchased from Sigma-Aldrich (Milwaukee, Wis.). Benzene-d6 (99.6% atom D, Sigma-Aldrich) for NMR spectroscopy of oxygen-sensitive species was degassed by three freeze-pump-thaw cycles prior to usage and stored over activated 4 Å molecular sieves. All other chemicals were purchased from Sigma-Aldrich (Milwaukee, Wis.), Alfa Aesar (Ward Hill, Mass.), TCI America (Portland, Oreg.), Oakwood Products, Inc. (West Columbia, S.C.), or GFS Chemicals (Columbus, Ohio).

[1] H NMR Spectra were obtained on either a Varian Mercury 300 (at 300 MHz) or Varian Inova 500 (at 500 MHz); $^{13}$C spectra were recorded on a Varian Mercury 300 (at 75 MHz) or a Varian Inova 500 (at 126 MHz); $^{31}$P spectra were recorded on either a Varian Mercury 300 (at 121 MHz) or a Varian Inova 500 (at 202 MHz). Chemical shifts ($^1$H and $^{13}$C) are reported in parts per million relative to TMS ($\delta$=0.00 ppm) and were referenced to the residual solvent peak; $^{31}$P NMR spectra were referenced to an external standard of 85% phosphoric acid ($\delta$=0.00 ppm). The following designations are used to describe multiplicities: s (singlet), d (doublet), t (triplet), q (quartet), br (broad), v (very), app (apparent). IR spectra were obtained on an Agilent Cary 630 FT-IR spectrometer equipped with an ATR accessory. Intensities are reported relative to the most intense peak of the spectrum and are defined as follows: w (weak, intensity between 0 and 33.3%), m (medium, between 33.3% and 66.6%), and s (strong, between 66.6% and 100%). Gas chromatography (GC) was performed on an Agilent 5870 GC (HP-5 column) with a flame ionization detector. GC/MS was performed on an Agilent 5870 GC (HP-5 ms column) with an Agilent 5975C MSD. Dodecane (99+%, Alfa Aesar) was used as an internal standard for quantitation. Exact masses (high resolution mass spectra) were obtained on a Bruker Daltonics APEX IV 4.7T FT-ICR spectrometer operating with electrospray ionization (ESI) in positive ion mode. Samples not suitable for ESI were ionized using an IonSense DART ion source operating in positive ion mode.

EXAMPLE 2

The following example describes the synthesis and use of a large number of nickel pre-catalysts.

Synthesis of the precatalyst complexes is straightforward (see FIG. 1): $NiCl_2 \cdot 6H_2O$ and the desired mono- or bidentate phosphine are combined in ethanol and briefly refluxed, after which the $L_2NiCl_2$ complex is isolated by a simple vacuum filtration on a sintered glass frit. After drying under vacuum to remove residual solvent, the complex is redissolved in THF or $CH_2Cl_2$ and 1 equiv of Grignard reagent (o-tolylmagnesium chloride, 2-mesitylmagnesium bromide, or similar) is added. Removal of the solvent by rotary evaporation and addition of methanol precipitates the complex and dissolves the magnesium chloride or bromide; isolation by vacuum filtration on a glass frit followed by washing with the appropriate solvent yields the complex in excellent purity. No further purification is necessary, though recrystallization can be carried out if desired.

A large number of complexes were prepared, with the most significant examples shown in Table 2. The selection of ligands encompasses a variety of mono- and bidentate phosphines commonly used in organic synthesis, as well as a number of less-frequently employed ligands. Many of the ligands in the latter category, particularly the low molecular weight, liquid phosphines, find only sporadic use in organic synthesis at least in part because they are difficult to synthesize and handle safely and because they are expensive to purchase due to the high cost of shipping pyrophoric and/or highly flammable goods. Triethylphosphine (110), dimethylphenylphosphine (108, 109), tricyclopentylphosphine (105), tri-n-butylphosphine (111), and tribenzylphosphine (106) all undergo reactions with air ranging from vigorous to violent, yet the precatalysts derived from each of these ligands are completely stable to oxygen in the solid phase and can be stored in air indefinitely.

In some instances, the complexes containing the o-tolyl moiety were not adequately stable to allow isolation in good yield and/or did not form air-stable complexes. For example, trans-$(PEt_3)_2$Ni(o-tolyl)Cl was isolated in good yield (>90%), however upon standing in air for several days, it begins to show clear signs of decomposition. A solution to this problem was found by increasing the steric bulk of the aryl group on nickel, which is hypothesized to further shield nickel from associative substitution.

To synthesize these complexes with more substituted aryl groups, the phosphine was condensed with $NiBr_2 \cdot 3H_2O$ to yield the corresponding $L_2NiBr_2$ complex, which was then treated with commercially available 2-mesitylmagnesium bromide. In this way, several complexes could be synthesized to form stable precatalysts. In the case of tri-n-butylphosphine, trans-$(Pn-Bu_3)_2$Ni(o-tolyl)Cl was found to be a liquid at room temperature that could not be stored for more than a few days, whereas trans-$(Pn-Bu_3)_2$Ni(2-mesityl)Br (111) is a stable solid. [dppp]Ni(o-tolyl)Cl and [dppb]Ni(o-tolyl)Cl were difficult to synthesize in good yield and purity. In both instances, the addition of a second equivalent of o-tolylmagnesium chloride takes place very readily (which lowers yield and purity of the isolated product) and neither is particularly stable in solution, leading to a loss of yield during workup and purification. In both instances, however, changing the aryl group to a mesityl group solved this problem, allowing isolation of cis-[dppp]Ni(2-mesityl)Br (113) and trans-[dppb]Ni(2-mesityl)Br (114).

The switch from o-tolyl to 2-mesityl did not enable isolation of a stable complex for: $PMe_2Ph$. Neither the o-tolyl nor the 2-mesityl complexes were stable under ambient conditions or in the presence of alcohols. Because $PMe_2Ph$ represents the least sterically demanding phosphine used in this study, it is perhaps unsurprising that its complex is in turn the most sensitive to nucleophilic attack by water or alcohols, since nickel is less shielded. As before, increasing the steric hindrance around nickel provided the solution. Reaction of trans-$(PMe_2Ph)_2NiBr_2$ with 2,4,6-triisopropylphenylmagnesium bromide yielded trans-$(PMe_2Ph)_2$Ni(2,4,6-triisopropylphenyl)Br 108 in 83% yield. This complex, in stark contrast to the corresponding o-tolyl and 2-mesityl complexes, demonstrates absolutely no air- or water sensitivity.

TABLE 2

Nickel Phosphine Complexes Synthesized[a]

| | | | Isolated yield (%) | | |
|---|---|---|---|---|---|
| Entry | Ligand | Complex | $L_nNiX_2$ | $L_nNi(R)X$[b] | overall |
| | Monodentate | | | | |
| 101 | PPh$_3$ | trans-(PPh$_3$)$_2$Ni(o-tolyl)Cl | 91 | 89 | 81 |
| 102 | PCyPh$_2$ | trans-(PCyPh$_2$)$_2$Ni(o-tolyl)Cl | 92 | 81 | 75 |

TABLE 2-continued

Nickel Phosphine Complexes Synthesized[a]

| | | | Isolated yield (%) | | |
|---|---|---|---|---|---|
| Entry | Ligand | Complex | $L_nNiX_2$ | $L_nNi(R)X$[b] | overall |
| 103 | PCy$_2$Ph | trans-(PCy$_2$Ph)$_2$Ni(o-tolyl)Cl | 95 | 88 | 84 |
| 104 | PCy$_3$ | trans-(PCy$_3$)$_2$Ni(o-tolyl)Cl | 97 | 87 | 84 |
| 105 | PCyp$_3$ | trans-(PCyp$_3$)$_2$Ni(o-tolyl)Cl | 99 | 90 | 89 |
| 106 | PBn$_3$ | trans-(PBn$_3$)$_2$Ni(o-tolyl)Cl | 96 | 90 | 86 |
| 107 | PPh$_2$Me | trans-(PMe$_2$Ph)$_2$Ni(o-tolyl)Cl | 99 | 81 | 80 |
| 108 | PMe$_2$Ph | trans-(PMe$_2$Ph)$_2$Ni(2,4,6-triisopropylphenyl)Br | 95 | 83 | 79 |
| 109 | PMe$_2$Ph | trans-(PMe$_2$Ph)$_2$Ni(2,6-dimethoxyphenyl)Br | 95 | 87 | 83 |
| 110 | PEt$_3$ | trans-(PEt$_3$)$_2$Ni(2-mesityl)Br | 95 | 88 | 84 |
| 111 | P(n-Bu)$_3$ | trans-(PnBu$_3$)$_2$Ni(2-mesityl)Br | 89 | 90 | 80 |
| Bidentate | | | | | |
| 112 | dppe | cis-[dppe]Ni(o-tolyl)Cl | 98 | 84 | 82 |
| 113 | dppp | cis-[dppp]Ni(2-mesityl)Br | 89 | 85 | 76 |
| 114 | dppb | trans-[dppb]Ni(2-mesityl)Br | 96 | 86 | 83 |
| 115 | (S)-(—)-BINAP | cis-[(S)-BINAP]Ni(o-tolyl)Cl | 94 | 97 | 91 |
| 116 | dppf | cis-[dppf]Ni(o-tolyl)Cl | 97 | 95 | 92 |
| 117 | dcpf | trans-[dcpf]Ni(o-tolyl)Cl | 98 | 83 | 81 |
| 118 | xantphos | trans-[xantphos]Ni(o-tolyl)Cl | 86 | 92 | 79 |
| 119 | pyphos | cis-[pyphos]Ni(o-tolyl)Cl | 90 | 82 | 74 |

[a]X = Cl or Br; dppe = 1,2-bis(diphenylphosphino)ethane; dppp = 1,3-bis(diphenylphosphino)propane; dppb = 1,4-bis(diphenylphosphino)butane; BINAP = 2,2'-bis(diphenylphosphino)-1,1'-binaphthyl; dppf = 1,1'-bis(diphenylphosphino)ferrocene; dcpf = 1,1'-bis(dicyclohexylphosphino)ferrocene; xantphos = 9,9-dimethyl-4,5-bis(diphenylphosphino)xanthene; pyphos = 2-[2-(diphenylphosphino)ethyl]pyridine.
[b]R = aryl group: o-tolyl, 2-mesityl, 2,4,6-triisopropylphenyl, or 2,6-dimethoxyphenyl.

However, due to the concern that activation of this precatalyst may be slow because of the extreme hindrance provided by the isopropyl groups at the 2- and 6-positions of the aryl ring, a precatalyst incorporating a 2,6-dimethoxyphenyl substituent (109) was also prepared and found to be air-stable.

As the numerous entries in Table 2 demonstrate, complexes of this type can be made from a wide range of phosphines, including electron rich and electron poor as well as sterically demanding and undemanding phosphines. However, a number of phosphines were challenging and did not necessarily provide the desired complex, such as electron poor and sterically hindered (P(4-F—C$_6$H$_4$)$_3$, P(o-tol)$_3$, and P(o-anis)$_3$) and extremely sterically hindered phosphines, regardless of their electronic nature (P(t-Bu)$_3$, (9,9-dimethyl-9H-xanthene-4,5-diyl)bis(di-tert-butylphosphine), and 1,2-bis((di-tert-butylphosphino)methyl)benzene). In all instances the L$_2$NiX$_2$ or LNiX$_2$ complexes formed in little or no yield, precluding attempts to synthesize the corresponding arylnickel complexes.

The structural features, geometry, and bonding, of the complexes were investigated. The complexes strongly favor a square planar arrangement, and whether the two phosphorus atoms are in a cis- or trans-arrangement at nickel is readily discerned from inspection of each complex's $^{31}$P NMR spectrum. Complexes derived from monodentate phosphines were generally found to adopt a trans geometry, as indicated by the presence of only one singlet in the $^{31}$P NMR spectrum. This arrangement presumably results from the minimization of steric interaction between the ligands on nickel. This steric repulsion is evidently large enough in magnitude to overwhelm any thermodynamic trans effects that might favor a cis arrangement.

Conversely, complexes derived from bidentate phosphines were more often observed to adopt a cis-arrangement, but several counterexamples were also seen. The preferred arrangement appeared to depend on the bite angle of the ligand, its rigidity, and the identity of the substituents on phosphorus.

For example, the complex derived from dppf (116) exists as the cis, square planar isomer in solution, whereas the closely related dcpf (117) adopts a distorted trans, square planar geometry, as illustrated in its single-crystal x-ray structure and in its $^{31}$P NMR spectrum. In this instance, the change from phenyl groups to cyclohexyl groups on phosphorus altered the preferred geometry, despite the fact that both complexes are built on the same ferrocene scaffold.

Figure 6:
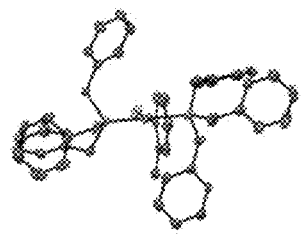
Figure 6:
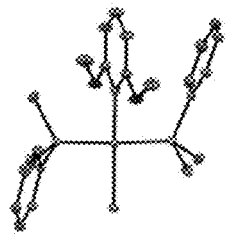
Figure 6:
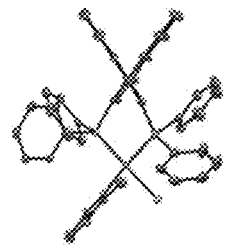
Figure 6:
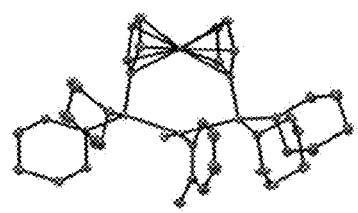
Figure 6:
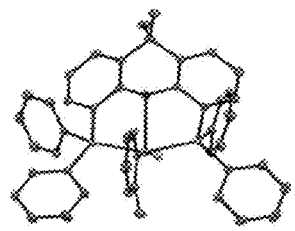
Figure 6:
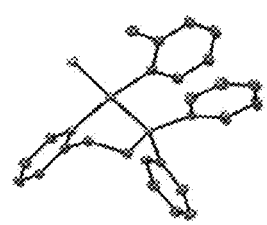

A selection of these precatalysts have been characterized by single-crystal X-ray diffraction (FIG. 6). Complexes derived from PBn$_3$ and PMe$_2$Ph both adopt nearly ideal trans, square planar structures, and are, for the most part, structurally unremarkable. Complex 115 (derived from (S)-BINAP) adopts a nearly ideal square planar structure with a cis arrangement, yielding a dihedral angle of 73.24(3)° between the two naphthalene rings of BINAP. The most interesting feature of this complex, though, is the fact that it forms diastereomers due to the two possible arrangements of the o-tolyl group. These diasteromers are both crystallographically and spectroscopically ($^1$H and $^{31}$P NMR) observable, suggesting interconversion is either slow or does not take place at any appreciable rate near room temperature. In FIG. 6. Complexes analyzed by single crystal X-ray diffraction. Thermal ellipsoids are drawn at 50% probability and hydrogen atoms are not included. Disorder of the o-tolyl ligand (106, 115, 118, 119) as well as solvent molecules of crystallization (106, 115, 117, 118) are not shown.

The complex derived from dcpf (117) is another interesting case: its $^{31}$P NMR spectrum exhibits one singlet despite the fact that it is a bidentate phosphine. XRD analysis showed a geometry at nickel that is best described as square planar, but with significant distortion toward tetrahedral. For example, the P(1)-Ni—P(2) bond angle is ca. 145°, well shy of the ideal 180°. However, the P(1)-Ni—Cl and P(2)-Ni—Cl bond angles are 91.264(13)° and 91.642(13)°, very close to the ideal 90° for square planar. Because of this, it is appropriate to describe the two phosphorus atoms as trans to one another.

Complex 118 (Xantphos) adopts a distorted square pyramidal geometry in the solid state. The oxygen of the ligand occupies the apical position and the two phosphorus atoms are in equatorial positions trans to each other. In solution, two isomers are observed by $^1$H and $^{31}$P NMR, the second perhaps being the true square planar isomer, without oxygen coordinated at nickel.

Pyphos (119), being an unsymmetrical, bidentate ligand, can form at least two structural isomers—chloride could be trans to either phosphorus or to nitrogen. The $^{31}$P NMR spectrum shows only one, sharp singlet, which suggests one isomer is dominant in solution. Single-crystal X-ray diffraction analysis showed 120 to adopt a square planar structure with chlorine trans to phosphorus. This geometrical arrangement presumably indicates that the thermodynamic trans effect dominates the ground-state conformation, rather than any potential steric interaction between the diphenylphosphino moiety and the o-tolyl ligand.

TABLE 3

Screening of the Ni-catalyzed Carbonyl-Ene Reaction[a]

n-Hex—CH=CH$_2$ + PhCHO $\xrightarrow[\text{PhMe, rt}]{\substack{\text{Ni catalyst} \\ \text{Et}_3\text{N (600 mol \%)} \\ \text{TESOTf (175 mol \%)}}}$ 120 allylic (n-Hex-C(OTES)=CH-CH$_2$-Ph) + 121 homoallylic (n-Pent-CH=CH-CH(OTES)-Ph)

| Entry | Ligand | Ni Source | Yield[b] (%) 120 | 121 | combined | Ratio 120:121 |
|---|---|---|---|---|---|---|
| 1 | PPh$_3$ | Ni(cod)$_2$ | 6 | 78 | 84 | 7:93 |
| 2 | PPh$_3$ | 101 | 7 | 81 | 88 | 8:92 |
| 3 | PCy$_2$Ph | Ni(cod)$_2$ | 52 | 21 | 73 | 71:29 |
| 4 | PCy$_2$Ph | 103 | 54 | 20 | 74 | 73:27 |
| 5 | PCyPh$_2$ | 102 | 17 | 56 | 73 | 23:77 |
| 6 | PCy$_3$ | 104 | 18 | 2 | 20 | 90:10 |
| 7 | PCyp$_3$ | 105 | 1 | nd | 1 | — |
| 8 | PBn$_3$ | 106 | 1 | 2 | 3 | 33:67 |
| 9 | (S)-(—)-BINAP | 115 | nd | 7 | 7 | — |

[a]See later table for complete data for all complexes. Reactions were carried out on 0.50 mmol scale with 20 mol % of catalyst and run for 48 hours.
[b]Yields determined by gas chromatography calibrated against an internal standard of n-dodecane.

To demonstrate the utility and advantages these precatalysts present over other means of entry into nickel(0), a nickel-catalyzed carbonyl-ene reaction was utilized, which couples a terminal alkene (or ethylene), an aldehyde, and a silyl triflate to form allylic or homoallyic silyl ethers (Table 3). Experiments demonstrated catalysts 103 and 101 were indeed catalytically competent and provided the desired allylic (120) and homoallylic (121) products, respectively. In both instances, the selectivity and yields were observed to be comparable to reactions using Ni(cod)$_2$. However, the rate was observed to be higher than when cod is present—reaction following studies demonstrated the reaction reaches completion in ca. 18 hours, rather than 36-48 hours which are required when using Ni(cod)$_2$ as the nickel source.

A comprehensive screen of every precatalyst prepared was carried out to demonstrate the ease with which screening of ligands can be accomplished (abbreviated results are shown in Table 4. Previously, Ni(cod)$_2$ would have to be weighed out for each reaction (in a glovebox) and each phosphine would have to be weighed or obtained via syringe. The use of single-component, air-stable precatalysts, however, reduces a screen of the selected phosphine ligands to a nearly trivial exercise which can be carried out on the benchtop with no exclusion of air during setup of the reactions.

CONCLUSION

A large number of air-stable Ni(II) complexes derived from a range of mono- and bidentate phosphine ligands used in synthesis were synthesized and characterized. These complexes are accessed from low-cost NiCl$_2$.6H$_2$O rather than from an expensive and air-sensitive Ni(0) source such as Ni(cod)$_2$. These complexes functioned as precatalysts for a huge range of nickel-catalyzed reactions, as they are readily converted to Ni(0) phosphine complexes by treatment with a range of reagents such as RMgX, RZnX, R$_3$B, RL$_1$, R$_3$SiH, and R$_3$SiOTf, allowing their convenient use in Ni(0)-catalyzed reactions. Many of these reactions, which previously employed Ni(cod)$_2$ as the Ni(0) source and thus required the use of a glovebox or glovebag, can now be carried out with no exclusion of air or water during setup, which greatly facilitates the use of nickel catalysis as a tool for synthesis. These benefits have been demonstrated in the context of the nickel-catalyzed carbonyl-ene reaction, where the use of a precatalyst provided a significant rate enhancement for the target reaction while maintaining equivalent selectivity to reactions catalyzed by Ni(cod)$_2$.

EXPERIMENTAL DATA

I. Materials, Methods, and General Considerations

Dichloromethane, THF, and acetonitrile were degassed by sparging with nitrogen and dried by passage through a column of activated alumina on an SG Water solvent purification system. Ethanol (200 proof, <0.1% water) and n-butanol (99.9%) were roughly degassed by sparging with nitrogen, and were not further dried prior to use. Methanol (>99.8%, <0.1% water) was used as received. Manipulation of all air-sensitive reagents was carried out in a glovebox (MBraun Unilab) filled with dry nitrogen. Thin-layer chromatography was carried out on EMD Millipore 60 F$_{254}$ glass-backed plates (250 μm coating thickness) and spots were visualized using UV light, basic potassium permanganate, ethanolic phosphomolybdic acid (PMA), or ceric ammonium nitrate (CAN) stains. Column chromatography was carried out on a Biotage Isolera flash chromatography system using SNAP KP-Sil columns (silica gel, 50 μm average particle size). Bis(1,5-cyclooctadiene)nickel(0) was purchased from Strem Chemicals (Newburyport, Mass.) and stored at −30° C. in a glovebox. All other chemicals were purchased from Sigma-Aldrich (Milwaukee, Wis.), Alfa Aesar (Ward Hill, Mass.), TCI America (Portland, Oreg.) or Oakwood Products, Inc. (West Columbia, S.C.).

NMR spectra were obtained in CDCl$_3$ (99.8% atom D), C$_6$D$_6$ (99.5% atom D), or CD$_2$Cl$_2$ (99.9% atom D) purchased from Cambridge Isotope Labs (Andover, Mass.). $^1$H NMR Spectra were obtained on a Varian Mercury 300 (at 300 MHz) or Varian Inova 500 (at 500 MHz); $^{13}$C spectra (when taken) were recorded on a Varian Inova 500 (at 126 MHz) with $^1$H decoupling; $^{31}$P spectra were recorded on a Varian Mercury 300 (at 121 MHz) or a Varian Inova 500 (at 202 MHz) with $^1$H decoupling. Chemical shifts ($^1$H and $^{13}$C) are reported in parts per million relative to TMS ($\delta$=0.00 ppm) and were referenced to the residual solvent peak ($^1$H CDCl$_3$ 7.26 ppm, C$_6$D$_6$ 7.16 ppm, CD$_2$Cl$_2$ 5.32 ppm; $^{13}$C CDCl$_3$ 77.16, C$_6$D$_6$ 128.06, CD$_2$Cl$_2$ 53.84); $^{31}$P NMR spectra are reported in parts per million relative to an external standard of 85% phosphoric acid ($\delta$=0.00 ppm). The following designations are used to describe multiplicities: s (singlet), d (doublet), t (triplet), q (quartet), p (pentet), br (broad), v (very), app (apparent). IR spectra were obtained on an Agilent Cary 630 FT-IR spectrometer equipped with an ATR accessory. Intensities are reported relative to the most intense peak of the spectrum and are defined as follows: w (weak, % T between 0 and 33.3%), medium (m, between 33.3% and 66.6%), and strong (s, between 66.6% and 100%). Melting points were determined on a MeI-Temp electrothermal apparatus using glass capillaries open to air except where specified.

Gas chromatography (GC) was performed on an Agilent 5870 GC (HP-5 column) with a flame ionization detector. GC/MS was performed on an Agilent 5870 GC (HP-5 ms column) with an Agilent 5975C quadrupole MSD. Dodecane (99+%, Alfa Aesar) was used as an internal standard for quantitation. Authentic samples of 120 and 121 (used for calibration curves and for comparison) were prepared by the previously published method (e.g. see Ng, S.-S., Ho, C.-Y., and Jamison, T. F. J. Am. Chem. Soc. 2006, 128, 11513-11528). Grignard reagents were titrated with salicylaldehyde phenylhydrazone and organolithium reagents were titrated with N-benzylbenzamide.

II. General Procedure for Synthesis of Complexes

L$_n$NiX$_2$:NiCl$_2$.6H$_2$O or NiBr$_2$.3H$_2$O, EtOH, and a magnetic stir bar were added to a round-bottom flask. The flask was sealed with a rubber septum, the solution was sparged with nitrogen for 15 minutes, the septum removed, and then the phosphine was added in one portion. The flask was fitted with a reflux condenser and the mixture was heated to 80° C. for 30 minutes, then allowed to cool to room temperature. Once cool, the flask was chilled to 0° C. for 10 minutes, after which the solid was collected by vacuum filtration, washed twice with ethanol (and twice with ether in some instances). Drying under vacuum yielded the product.

L$_n$(aryl)NiX$_2$: L$_n$NiX$_2$ was added to an oven-dried round-bottom flask containing a magnetic stir bar. Solvent (THF of CH$_2$Cl$_2$) was added, the solution was cooled to 0° C. with an ice bath, and Grignard reagent was added dropwise with vigorous stirring. The solution was allowed to stir for 15 minutes at 0° C., after which the stir bar was removed and the solution was evaporated to dryness under reduced pressure. MeOH was added and the mixture was sonicated until a uniform suspension was obtained (approx. 5 minutes). After cooling to 0° C., the precipitate was collected by vacuum filtration, washed with two portions of cold MeOH, and dried under high vacuum to yield the complex.

III. Procedure for Carbonyl Ene reaction

A 1 dram vial was charged with a magnetic stir bar, the desired precatalyst (0.10 mmol), 1-octene (2.5 mmol, 427 μL), triethylamine (3 mmol, 418.1 μL), benzaldehyde (0.50 mmol, 50.8 μL), toluene (2 mL), and dodecane (50.0 μL). This mixture was stirred for ca. 30 seconds, after which TESOTf (0.875 mmol) was added. The vial was sealed with a PTFE-lined screw cap and allowed to stir at room temperature. After the desired length of time (48 hours for all screening reactions), the reaction mixture was quenched by addition of 500 μL of methanol. Approximately 100 μL of the crude reaction mixture was then diluted into 1 mL of EtOAc and the solution analyzed by GC.

TABLE 5

Complete Screening Data for Carbonyl Ene Reaction[a]

| Entry | Ligand | Ni Source | Yield[b] (%) 120 | 121 | combined | Ratio 120:121 |
|---|---|---|---|---|---|---|
| 1 | PPh$_3$ | 101 | 7 | 81 | 88 | 8:92 |
| 1a | PPh$_3$ | Ni(cod)$_2$ | 6 | 78 | 84 | 7:93 |
| 2 | PCyPh$_2$ | 102 | 17 | 56 | 73 | 23:77 |
| 3 | PCy$_2$Ph | 103 | 54 | 20 | 74 | 73:27 |
| 3a | PCy$_2$Ph | Ni(cod)$_2$ | 52 | 21 | 73 | 71:29 |
| 4 | PCy$_3$ | 104 | 18 | 2 | 20 | 90:10 |
| 5 | PCyp$_3$ | 105 | 1 | nd | 1 | — |
| 6 | PBn$_3$ | 106 | 1 | 2 | 3 | 33:67 |
| 7 | PPh$_2$Me | 107 | nd | nd | — | — |
| 8 | PMe$_2$Ph | 108 | nd | nd | — | — |
| 9 | PMe$_2$Ph | 109 | nd | nd | — | — |
| 10 | PEt$_3$ | 110 | nd | nd | — | — |
| 11 | P(n-Bu)$_3$ | 111 | nd | nd | — | — |
| 12 | dppe | 112 | nd | 2 | 2 | — |
| 13 | dppp | 113 | nd | 2 | 2 | — |
| 14 | dppb | 114 | nd | nd | — | — |
| 15 | (S)-(—)-BINAP | 115 | nd | 7 | 7 | — |
| 16 | dppf | 116 | nd | nd | — | — |
| 17 | dcpf | 117 | nd | nd | — | — |
| 18 | xantphos | 118 | nd | nd | — | — |
| 19 | pyphos | 119 | nd | 6 | 6 | — |

[a]Reactions were carried out on 0.50 mmol scale with 20 mol % of catalyst and run for 48 hours.
[b]Yields determined by gas chromatography calibrated against an internal standard of n-dodecane.

III. Synthesis and Characterization of Complexes 101, 102, and 104

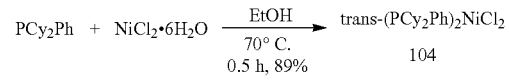

trans-bis(dicyclohexylphenylphosphine)nickel(II) chloride (104, Method A). To a 25 mL round-bottom flask equipped with a magnetic stir bar was added NiCl$_2$.6H$_2$O (0.50 mmol, 119 mg) and PCy$_2$Ph (1.05 mmol, 288 mg). Ethanol (10 mL) was added, the flask fitted with a reflux condenser, placed under an atmosphere of argon, and the mixture was heated to 70° C. After 30 minutes, the mixture was cooled to 0° C. with a water-ice bath and the solid collected by vacuum filtration. The solid was washed twice with cold ethanol (5 mL) and twice with cold ether (5 mL). Drying under vacuum yielded 104 (302 mg, 89%) as a fine, purple powder.

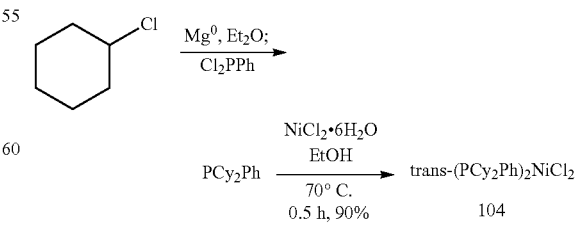

trans-bis(dicyclohexylphenylphosphine)nickel(II) chloride (104, Method B). An oven dried, 500 mL, two-neck, round-bottom flask was charged with a magnetic stir bar and magnesium turnings (251 mmol, 6.10 g), fitted with a reflux condenser and rubber septum, and the apparatus thoroughly flushed with argon. Diethyl ether (50 mL) was transferred to the flask along with a single crystal of iodine. The septum was removed and replaced with a dropping funnel containing chlorocyclohexane (254 mmol, 30.10 mL) in 250 mL of anhydrous diethyl ether. Approximately 15 mL of this chlorocyclohexane solution was added to the flask, which was then gently warmed with a heating mantle to initiate the reaction, as indicated by disappearance of the iodine color and mild bubbling of the ether. Following initiation, the chlorocyclohexane solution was added at such a rate so as to keep the solution at a moderate reflux without external heating (ca. 1-2 drops per second). After complete addition of the chlorocyclohexane solution, the mixture was heated to reflux for 1 hour, after which the flask was cooled to −30° C. and a solution of phenyldichlorophosphine (100 mmol, 13.57 mL) in 100 mL of diethyl ether was added dropwise with vigorous stirring. After addition of the phenyldichlorophosphine, the solution was allowed to warm to room temperature and stirred for 1 hour. The reaction was quenched with saturated aqueous ammonium chloride and the ether layer washed twice with water. The ether was evaporated under reduced pressure and 200 mL of ethanol were added, followed by $NiCl_2 \cdot 6H_2O$ (45 mmol, 10.70 g), after which the solution was heated to 70° C. for 30 minutes. The mixture was cooled to 0° C. with a water-ice bath and the solid collected by vacuum filtration. The solid was washed with two 15 mL portions of cold ethanol and two 15 mL portions of diethyl ether. The solid was collected and dried under vacuum for several hours to yield 104 (27.46 g, 90%) as a fine, purple powder.

Characterization of 104: mp 225-226° C. dec (e.g., see Stone, P. J. and Zvi, D. Inorg. Chim. Acta 1970, 5, 434-438. Samples prepared by Methods A and B, neither of which had been recrystallized, both melted at 225-226° C. dec; 226-228° C. dec). $^1H$ NMR (500 MHz, $C_6D_6$) δ 7.80 (d, J=7.6 Hz, 4H), 7.27 (t, J=7.5 Hz, 4H), 7.00 (t, J=7.5 Hz, 2H), 3.59 (br s, 4H), 2.52 (d, J=10.7 Hz, 4H), 2.05 (q, J=11.5, 11.0 Hz, 4H), 1.96-1.72 (m, 16H), 1.61 (d, J=10.0 Hz, 4H), 1.32 (q, J=12.5 Hz, 4H), 1.25-1.10 (m, 8H). $^1H$ NMR (500 MHz, $CD_2Cl_2$) δ 7.82 (app s, 4H), 7.43 (app s, 4H), 7.09 (app s, 2H), 2.57-2.12 (m, 8H), 1.89 (d, J=12.6 Hz, 4H), 1.80-1.61 (m, 12H), 1.56 (q, J=11.8, 4H), 1.42-1.28 (m, 12H), 1.22 (q, J=12.8 Hz, 4H). $^{13}C\{^1H\}$ NMR (126 MHz, $CD_2Cl_2$) δ 131.80 (br s), 127.46, 31.70 (br s), 30.09 (br s), 28.00, 27.12. $^{31}P\{^1H\}$ (121 MHz, $CD_2Cl_2$) ca. 25 (v br s). See discussion below for details. IR (ATR, $cm^{-1}$): 3075 (w), 3051 (w), 2928 (s), 2850 (m), 1445 (m), 1434 (s), 1294 (w), 1266 (w), 1199 (w), 1186 (w), 1171 (m), 1111 (m), 1098 (w), 999 (m), 914 (w), 895 (w), 887 (w), 846 (m), 818 (w), 740 (s), 697 (s), 688 (s). Crystals suitable for single-crystal X-ray diffraction analysis were obtained by slow evaporation (at room temperature) of a THF/ethanol solution of the complex. Slow evaporation of THF/isopropanol, benzene/ethanol, and benzene/isopropanol solutions also yielded satisfactory crystals.

Initial attempts to characterize 104 by $^{31}P$ NMR spectroscopy showed no signals, even after several hundred transients on a $CD_2Cl_2$ solution nearly saturated with 104. Further attempts to obtain a spectrum, including collecting an even larger number of transients, yielded a spectrum with an extremely broad signal centered at approximately 25 ppm spanning from ca. 120 to −70 ppm and two small singlets, one at 3.13 ppm ($PCy_2Ph$) and one at 45.59 ($OPCy_2Ph$). The presence of these two signals suggests some decomposition of the complex (caused by oxygen—a J-Young tube was not used) in the time required to obtain the spectrum, which was several hours. The location of the peak's maximum is very sensitive to the phasing of the spectrum, so determination of a precise chemical shift is not possible. Given the appearance of the $^1H$ and $^{13}C$ spectra, which have multiple broadened signals, it is apparent that the proximity to the nickel atom is allowing very rapid relaxation for some atoms of the complex, causing severe broadening. Since the phosphorus atoms are directly bonded to nickel, it is not surprising that they experience this effect to a greater extent. These results were verified on several different spectrometers to rule out hardware or acquisition problems.

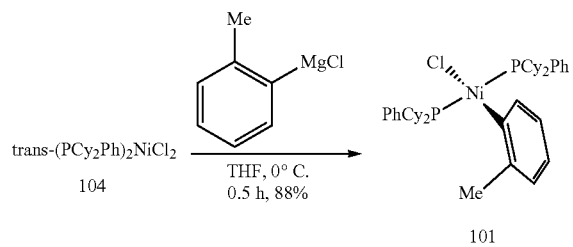

trans-bis(dicyclohexylphenylphosphine) nickel(o-tolyl) chloride (101): trans-$(PCy_2Ph)_2NiCl_2$ (104, 15.46 mmol, 10.49 g) was added to an oven-dried, round-bottom flask with a magnetic stir bar. Tetrahydrofuran (250 mL) was added and the mixture stirred for 10 minutes. This homogeneous solution was cooled to 0° C. with an ice bath and o-tolylmagnesium chloride (15.46 mmol, 0.865 M in THF, 17.87 mL) was added dropwise at a rate of ca. 2 drops per second with vigorous stirring. Near the end of the addition, the solution began to lighten in color from dark purple to red-orange. The solution was allowed to stir for 30 minutes at 0° C., after which anhydrous methanol (15 mL) was added to quench any unreacted Grignard reagent. The stir bar was removed and the solution was evaporated to dryness under reduced pressure. Anhydrous methanol (100 mL) was added and the mixture was sonicated until a uniform, yellow suspension with no large aggregates was obtained (approx. 15 minutes). After cooling to 0° C., the yellow precipitate was collected by vacuum filtration, washed with two portions of cold methanol, and dried under high vacuum to yield 101 (9.97 g, 88%) as a fine, yellow powder.

Characterization of 101: mp 149-150° C. dec. $^1H$ NMR (500 MHz, $C_6D_6$) δ 7.49 (s, 4H), 7.10 (app s, 7H), 6.76-6.58 (m, 3H), 3.51 (s, 3H), 2.52 (s, 4H), 2.42-2.21 (m, 4H), 1.95-0.83 (m, 36H). $^{13}C\{^1H\}$ NMR (126 MHz, $C_6D_6$) δ 149.86 (t, J=32.3 Hz), 142.76, 138.45, 132.91, 130.70 (t, J=15.5 Hz), 127.09, 124.17, 122.27, 33.90 (t, J=9.8 Hz), 33.32 (t, J=9.7 Hz), 30.25 (d, J=21.6 Hz), 29.47 (d, J=7.5 Hz), 28.28 (t, J=5.3 Hz), 28.09 (t, J=6.2 Hz), 27.88 (t, J=5.2 Hz), 27.66, 26.79 (d, J=7.3 Hz). $^{31}P\{^1H\}$ (202 MHz, $C_6D_6$): 16.09 (s). $^{31}P\{^1H\}$ (202 MHz, $CD_2Cl_2$): 15.00 (s), 44.89 (s), 3.13 (s). 3049 (w), 2922 (m), 2852 (m), 1570 (w), 1561 (w), 1447 (m), 1432 (m), 1326 (w), 1296 (w), 1264 (m), 1203 (w), 1178 (w), 1115 (w), 1027 (w), 1003 (m), 917 (w), 889 (w), 848 (m), 731 (s), 695 (s). HRMS (ESI, m/z): $[M+H]^+$ calcd for $C_{43}H_{61}ClNiP_2$, 733.3363; found, 733.3354. $[M-Cl]^+$ calcd for $C_{43}H_{61}ClNiP_2$, 697.3596; found, 697.3592. Crystals suitable for single-crystal X-ray diffraction analysis were obtained by the slow evaporation (at room temperature) of a THF solution of the complex. An ether solution also yielded high-quality crystals.

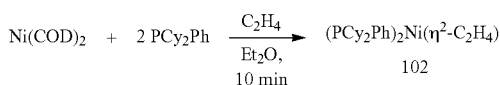

ethylenebis(dicyclohexylphenylphosphine)nickel(0) (102): In a glovebox, Ni(COD)$_2$ (2.00 mmol, 0.550 g) and PCy$_2$Ph (4.00 mmol, 1.098 g) were combined in a 20 mL vial with a magnetic stir bar and diethyl ether (12 mL) was added, yielding an intensely colored, dark red solution. After stirring for 10 minutes, ethylene was bubbled through the solution, causing a rapid change in the color to orange and subsequently to bright yellow. Ethylene was bubbled through the solution for an additional 10 minutes, after which the vial was sealed and allowed to stand at −20° C. to complete the precipitation. The precipitate was collected by vacuum filtration and washed with two small portions of cold diethyl ether. Drying under vacuum yielded the complex as a fine, yellow powder (1.048 g, 86%). $^1$H NMR (300 MHz, C$_6$D$_6$) δ 7.65-7.56 (m, 4H), 7.09-7.00 (m, 6H), 2.43 (s, 4H), 2.33-2.19 (m, 4H), 2.19-2.06 (m, 4H), 2.00-1.84 (m, 4H), 1.77-1.61 (m, 8H), 1.61-1.50 (m, 4H), 1.50-1.37 (m, 4H), 1.37-1.10 (m, 12H), 1.09-0.91 (m, 4H). $^{13}$C{$^1$H} NMR (126 MHz, C$_6$D$_6$) δ 134.85 (dd, J=10.9, 8.2 Hz), 133.99 (t, J=6.0 Hz), 127.18 (t, J=3.9 Hz), 39.69 (t, J=6.3 Hz), 35.18 (dd, J=10.8, 9.7 Hz), 30.20 (t, J=3.2 Hz), 29.54, 27.92 (t, J=6.0 Hz), 27.62 (t, J=4.3 Hz), 26.87. $^{31}$P{$^1$H} NMR (121 MHz, C$_6$D$_6$): 37.6 ppm. IR (ATR, cm$^{-1}$): 3074 (w), 3047 (w), 2922 (s), 2848 (m), 1481 (w), 1445 (m), 1434 (m), 1335 (w), 1270 (w), 1203 (w), 1180 (m), 1111 (w), 1001 (m), 882 (s), 848 (m), 742 (s), 697 (s).

Section IV. Procedures for Nickel-catalyzed Benzylation Reactions

General Procedure A: To an 8 mL screw-top vial containing a magnetic stir-bar was added precatalyst 101 (0.050 mmol, 36.7 mg), alkene (5.00 mmol), triethylamine (6.00 mmol, 836 μL), the benzyl chloride (1.00 mmol), and CH$_2$Cl$_2$ (500 μL). After stirring the mixture for a few seconds, silyl triflate (1.5 mmol) was added, the vial capped, and left to stir for 4 to 8 hours as indicated. After the necessary time had elapsed, the reaction mixture was allowed to stir open to the air for 5 minutes, after which it was passed through a 4 cm plug of silica gel (pre-wetted with dichloromethane). The silica gel plug was washed with 25 mL of dichloromethane followed by 25 mL of a 1:1 mixture of hexanes/ethyl acetate. After concentration under reduced pressure, the crude material was purified by column chromatography on silica gel with the indicated eluent.

General Procedure B (modification for substrates with free —OH, —NH$_2$, —CO$_2$H groups): To an 8 mL screw-top vial containing a magnetic stir-bar was added alkene (3.00-5.00 mmol), triethylamine (6.00-12.00 mmol), the benzyl chloride (1.00 mmol), and CH$_2$Cl$_2$ (500 μL). The mixture was cooled to 0° C., after which the appropriate silyl triflate (4.50-10.00 mmol) was added dropwise. After the addition was complete, the mixture was warmed to room temperature, precatalyst 101 (0.050 mmol, 36.7 mg) was added, the vial was closed with a screw-cap, and the mixture was stirred at room temperature for 4 to 8 hours as indicated. Work-up and purification were carried out as indicated for each substrate.

General Procedure C (modification for reactions run with precatalyst 102): In a glovebox, precatalyst 102 (0.05 mmol, 31.8 mg) was added to an 8 mL screw-top vial containing a magnetic stir-bar. To the catalyst was added alkene (5.00 mmol), triethylamine (6.00 mmol, 836 μL), the benzyl chloride (1.00 mmol), and toluene (500 μL). After briefly stirring the mixture, silyl triflate (1.5 mmol) was added, the vial capped, and left to stir for the indicated length of time (12-24 hours). After this length of time, the reaction was worked up and purified as in General Procedure A.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A pre-catalyst, comprising:
a nickel (II) atom, wherein the nickel (II) atom is associated with at least one phosphine ligand; at least one aryl ligand; and at least one leaving group, wherein one or more of the ligands is chiral.

2. The pre-catalyst of claim 1, wherein the pre-catalyst comprises two phosphine ligands.

3. The pre-catalyst of claim 1, wherein the pre-catalyst comprises two phosphine ligands, one aryl ligand, and one leaving group.

4. The pre-catalyst of claim 2, wherein the two phosphine ligands are trans.

5. The pre-catalyst of claim 2, wherein the two phosphine ligands are cis.

6. The pre-catalyst of claim 2, the two phosphine ligands are monodentate.

7. The pre-catalyst of claim 1, wherein the pre-catalyst has the structure:

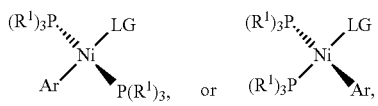

wherein each $R^1$ is independently optionally substituted alkyl, optionally substituted cycloalkyl, or optionally substituted aryl, or any two $R^1$ may be joined together to form a ring;
Ar is the at least one aryl ligand, and LG is the at least one leaving group.

8. The pre-catalyst of claim 1, wherein the pre-catalyst has the structure:

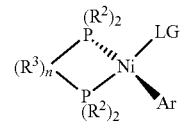

wherein each $R^2$ is independently optionally substituted alkyl, optionally substituted cycloalkyl, or optionally substituted aryl, or any two $R^2$ are joined together to form a ring;
each $R^3$ is —O—, optionally substituted alkylene, optionally substituted heteroalkylene, optionally substituted arylene, optionally substituted heteroarylene, or optionally substituted ferrocenylene;
n is 1, 2, 3, 4, 5, or 6; Ar is the at least one aryl ligand; and LG is the at least one leaving group.

9. The pre-catalyst of claim 1, wherein the pre-catalyst is not:

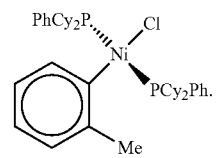

10. A pre-catalyst, comprising:
a nickel (II) atom, wherein the nickel (II) atom is associated with at least one N-heterocyclic carbene ligand; at least one aryl ligand; and at least one leaving group.

11. The pre-catalyst of claim 10, wherein the pre-catalyst further comprises at least one phosphine ligand.

12. The pre-catalyst of claim 10, wherein the pre-catalyst comprises one heterocyclic carbene ligand, one phosphine ligand, one aryl ligand, and one leaving group.

13. The pre-catalyst of claim 11, wherein the phosphine ligand is monodentate.

14. The pre-catalyst of claim 1, wherein each monodentate phosphine ligand is the same or different and has the structure $P(R^1)_3$, wherein each $R^1$ is independently optionally substituted alkyl, optionally substituted cycloalkyl, or optionally substituted aryl.

15. The pre-catalyst of claim 1, wherein the pre-catalyst comprises a bidentate phosphine ligand.

16. The pre-catalyst of claim 15, wherein the bidentate phosphine ligand has the structure $(R^2)_2P—(R^3)_n—P(R^2)_2$, wherein each $R^2$ is independently optionally substituted alkyl, optionally substituted cycloalkyl, or optionally substituted aryl, or any two $R^2$ can be joined together to form a ring; each $R^3$ is —O—, optionally substituted alkylene, optionally substituted heteroalkylene, optionally substituted arylene, optionally substituted heteroarylene, or optionally substituted ferrocenylene; and n is 1, 2, 3, 4, 5, or 6.

17. The pre-catalyst of claim 1, wherein the aryl ligand is substituted at one or both ortho positions.

18. The pre-catalyst of claim 1, wherein the leaving group is selected from the group consisting of halo, OTs, and OMs.

19. A method, comprising:
activating a pre-catalyst as in claim 1 to form a catalyst.

20. A compound selected from the group consisting of trans-$(PPh_3)_2$Ni(o-tolyl)Cl, trans-$(PCyPh_2)_2$Ni(o-tolyl)Cl, trans-$(PCy_2Ph)_2$Ni(o-tolyl)Cl, trans-$(PCy_3)_2$Ni(o-tolyl)Cl, trans-$(PCy_3)_2$Ni(o-tolyl)Cl, trans-$(PCy_3)_2$Ni(o-tolyl)Cl, trans-$(PCyp_3)_2$Ni(o-tolyl)Cl, trans-$(PCyp_3)_2$Ni(o-tolyl)Cl, trans-$(PBn_3)_2$Ni(o-tolyl)Cl, trans-$(PBn_3)_2$Ni(o-tolyl)Cl, trans-$(PMe_2Ph)_2$Ni(o-tolyl)Cl, trans-$(PMe_2Ph)_2$Ni(2,4,6-triisopropylphenyl)Br, trans-$(PMe_2Ph)_2$Ni(2,6-dimethoxyphenyl)Br, trans-$(PEt_3)_2$Ni(2-mesityl)Br, trans-$(PnBu_3)_2$Ni(2-mesityl)Br, cis-[dppe]Ni(o-tolyl)Cl, cis-[dppp]Ni(2-mesityl)Br, trans-[dppb]Ni(2-mesityl)Br, cis-[(S)-BINAP]Ni(o-tolyl)Cl, cis-[dppf]Ni(o-tolyl)Cl, trans-[dcpf]Ni(o-tolyl)Cl, trans-[xantphos]Ni(o-tolyl)Cl, and cis-[pyphos]Ni(o-tolyl)Cl, wherein:

Cy is cyclohexyl,
Cyp is cyclopentyl,
Bn is benzyl,
dppe is 1,2-bis(diphenylphosphino)ethane,
dppp is 1,3-bis(diphenylphosphino)propane,
dppb is 1,4-bis(diphenylphosphino)butane,
BINAP is 2,2'-bis(diphenylphosphino)-1,1'-binaphthyl,
dppf is 1,1'-bis(diphenylphosphino)ferrocene,
dcpf is 1,1'-bis(dicyclohexylphosphino)ferrocene,
xantphos is 9,9-dimethyl-4,5-bis(diphenylphosphino)xanthene, and
pyphos is 2-[2-(diphenylphosphino)ethyl]pyridine.

21. The compound of claim 20, wherein the compound is trans-$(PCy_3)_2$Ni(o-tolyl)Cl, wherein Cy is cyclohexyl.

22. The compound of claim 20, wherein the compound is trans-$(PCy_2Ph)_2$Ni(o-tolyl)Cl, wherein Cy is cyclohexyl.

23. The compound of claim 20, wherein the compound is trans-$(PCyp_3)_2$Ni(o-tolyl)Cl, wherein Cyp is cyclopentyl.

24. The compound of claim 20, wherein the compound is trans-$(PEt_3)_2$Ni(2-mesityl)Br.

25. The compound of claim 20, wherein the compound is trans-$(PBn_3)_2$Ni(o-tolyl)Cl, wherein Bn is benzyl.

26. The compound of claim 20, wherein the compound is trans-$(PPh_2Me)_2$Ni(o-tolyl)Cl.

27. The compound of claim 20, wherein the compound is cis-(dppe)Ni(o-tolyl)Cl, wherein dppe is 1,2-bis(diphenylphosphino)ethane.

28. The compound of claim 20, wherein the compound is cis-[(S)-BINAP)]Ni(o-tolyl)Cl, wherein BINAP is 2,2'-bis(diphenylphosphino)-1,1'-binaphthyl.

29. A method, comprising:
activating a pre-catalyst as in claim 20 to form a catalyst.

* * * * *